US011578125B2

(12) United States Patent
Nevanen et al.

(10) Patent No.: US 11,578,125 B2
(45) Date of Patent: Feb. 14, 2023

(54) ANTI-THYROID HORMONE (T4) RECOMBINANT ANTIBODY OR ANTIGEN BINDING FRAGMENT

(71) Applicants: Teknologian tutkimuskeskus VTT Oy, Espoo (FI); Politecnico di Milano, Milan (IT)

(72) Inventors: Tarja Nevanen, Vtt (FI); Henri Arola, Vtt (FI); Antti Tullila, Vtt (FI); Juha Rouvinen, Kuopio (FI); Tarja Parkkinen, Kuopio (FI); Pierangelo Metrangolo, Milan (IT)

(73) Assignees: Teknologian tutkimuskeskus VTT Oy, Epoo (FI); Politecnico di Milano, Milan (IT)

( * ) Notice: Subject to any disclaimer, the term of this patent is extended or adjusted under 35 U.S.C. 154(b) by 0 days.

(21) Appl. No.: 17/059,268

(22) PCT Filed: May 28, 2019

(86) PCT No.: PCT/FI2019/050408
§ 371 (c)(1),
(2) Date: Nov. 27, 2020

(87) PCT Pub. No.: WO2019/229296
PCT Pub. Date: Dec. 5, 2019

(65) Prior Publication Data
US 2021/0230270 A1      Jul. 29, 2021

(30) Foreign Application Priority Data

May 29, 2018 (FI) ...................................... 20185486

(51) Int. Cl.
*C07K 16/26* (2006.01)
(52) U.S. Cl.
CPC .......... *C07K 16/26* (2013.01); *C07K 2317/55* (2013.01); *C07K 2317/92* (2013.01)
(58) Field of Classification Search
None
See application file for complete search history.

(56) References Cited

U.S. PATENT DOCUMENTS

2017/0355756 A1 * 12/2017 Julien ...................... A61P 25/28

FOREIGN PATENT DOCUMENTS

| EP | 0168907 | | 11/1992 |
| EP | 1207393 | | 5/2002 |
| EP | 2516470 | | 2/2018 |
| JP | 2010178649 A | | 8/2010 |
| WO | WO 2008068048 | * | 6/2008 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Kamrun, Nahar Islam et al.: "Direct Construction of an Open-Sandwich Enzyme Immunoassay for One-Step Noncompetitive Detection of Thyroid Hormone T4", Analytical Chemistry, vol. 83, No. 3, Feb. 1, 2011 (Feb. 1, 2011), pp. 1008-1014, XP055608405, US, Materials and methods; figure all; example all.
Anonymous: "In Vitro & Ex Vivo Assays for Identification of Modulators of Thyroid Hormone Signalling", Nov. 10, 2013 (Nov. 10, 2013), XP055608627, Retrieved from the Internet: URL:http://www.oecd.org/env/ehs/testing/Thyroid_scoping_Part_1.pdf [retrieved on Jul. 24, 2019] p. 12; figure all; example all.
Thienpont, Benedicte et al.: "Zebrafish Eleutheroembryos Provide a Suitable Vertebrate Model for Screening Chemicals that Impair Thyroid Hormone Synthesis", Environmental Science & Technology, vol. 45, No. 17, Jul. 29, 2011 (Jul. 29, 2011), pp. 7525-7532, XP055606626, US, ISSN: 0013-936X, DOI: 10.1021/es202248h, figure 1; example all.
Calsolaro, Valeria et al: "Thyroid Disrupting Chemicals", International Journal of Molecular Sciences, vol. 18, No. 12., Dec. 1, 2017 (Dec. 1, 2017), p. 2583, XP065608629, DOI: 10.3390/ijms18122583, table 1.
Yen, Paul M. Physiological Reviews, vol. 81, No. 3, Jul. 2001, "Physiological and Molecular Basis of Thyroid Hormone Action", pp. 1097-1142.
Thyroxine Antibody (20C-CR1053R). Rabbit polyclonal Thyroxine antibody. Data Sheet. [online]. Fitzgerald Industries, 2018, [retrieved on Dec. 3, 2018] Retrieved from https://www.fitzgerald-fii.eu/thyroxine-antibody-20c-cr1053r.html.

(Continued)

*Primary Examiner* — Adam Weidner
(74) *Attorney, Agent, or Firm* — Meunier Carlin & Curfman LLC

(57) ABSTRACT

The present invention relates to the fields of antibodies, antigen binding fragments and immunodiagnostics. Specifically, the invention relates to a recombinant anti-body or antigen binding fragment for binding thyroid hormone T4 (thyroxine) and halogenated bisphenol A. Also, the present invention relates to an isolated nucleic acid molecule comprising a nucleotide sequence that encodes the recombinant antibody or antigen binding fragment of the present invention, as well as an ex-pression vector and host cell comprising the nucleic acid molecule of the present invention. Still, the present invention relates to a method of producing a recombi-nant antibody or antigen binding fragment for binding T4 thyroid hormone and hal-ogenated bisphenol A, a test kit and an immunoassay comprising the recombinant antibody or antigen binding fragment of the present invention, and a method for determining T4 thyroid hormone and/or halogenated bisphenol A levels in a sam-ple of a subject. Still further, the present invention relates to a method of treating a sample, e.g. an immunoaffinity-based sample preparation method for enrich-ment of the halogenated bisphenol A from a sample.

12 Claims, 8 Drawing Sheets
Specification includes a Sequence Listing.

(56) References Cited

OTHER PUBLICATIONS

Tullila, Antti and Nevanen, Tarja K.: "Utilization of Multi-Immunization and Multiple Selection Strategies for Isolation of Hapten-Specific Antibodies from Recombinant Antibody Phage Display Libraries", Published May 31, 2017, International Journal of Molecular Sciences 18(6), 1169, 15 pages.

Pulli, Timo, Höyhtyä, Matti, Söderlund, Hans, Takkinen, Kristiina: "One-Step Homogeneous Immunoassay for Small Analytes", Anal. Chem. 2005, 77, pp. 2637-2642.

Takkinen, K. et al.: "An active single-chain antibody containing a cellulase linker domain is secreted by *Escherichia coli*". Protein Engineering, vol. 4, No. 7, pp. 837-841, 1991.

Nieba, Lars et al.:"Competition BIAcore for measuring True Affinities: Large Differences from Values Determined from Binding Kinetics", 1996, Anal. Biochem. 234, pp. 155-165 (1996) Article No. 0067.

Badescu, George O. et al.: "Kinetic Characterisation of a Single Chain Antibody against the Hormone Abscisic Acid: Comparison with Its Parental Monoclonal", Mar. 29, 2016, Plos One, pp. 1-14.

Persson, David B. et al.: "An Arginine Switch in the Species B Adenovirus Knob Determines High-Affinity Engagement of Cellular Receptor CD46v". Journal of Virology, Jan. 2009, vol. 83, No. 2, pp. 673-686.

Adamczyk, M. et al.: "Immunoassay Reagents for Thyroid Testing. 3. Determination of the Solution Binding Affinities of a T4 Monoclonal Antibody Fab Fragment for a Library of Thyroxine Analogs Using Surface Plasmon Resonance", Bioconjugate chemistry, 1998, 9, pp. 23-32.

Cannon, Michelle et al.: "Comparative analyses of a small molecule/enzyme interaction by multiple users of Bioacore technology", Analytical Biochemistry, 330 (2004), pp. 98-113.

McCoy, Airlie J. et al.: "Phaser crystallographic software", J. Appl. Cryst. vol. 40, Part 4. Aug. 2007, pp. 658-674.

Emsley, P. et al.: "Features and development of Coot", Acta Cryst. Section D 66, Biological Crystallography, pp. 468-501, (2010).

Adams, Paul D. et al.: "Phenix: a comprehensive Python-based system for macromolecular structure solution", Acta Crystallographica Section D 66, Biological Crystallography, pp. 213-221 (2010).

McIver, C. R. et al.: "Can thyroid hormone mimics affect thyroid hormone measurement by immunoassay?", Elsevier, The Canadian Society of Clinical Chemists, Clinical Biochemistry vol. 46. Sep. 2013, No. 13-14, pp. 1302-1304.

Marchesini, G. R. et al. "Biosensor Recognition of Thyroid-Disrupting Chemicals Using Transport Proteins". Analytical Chemistry, Feb. 15, 2006, vol. 78, No. 4, pp. 1107-1114.

Li, Yu et al. "Development of an immunochromatographic test strip and ic-ELISA for tetrabromobisphenol: a detection in lake water and rice pudding samples". Food and Agricultural Immunology, 2016, vol. 27, No. 4, pp. 460-470.

Cristina Caldas et al: "Humanization of the anti-CD18 antibody 6.7: an unexpected effect of a framework residue in binging to antigen.", Molecular immunology, vol. 39, No. 15, May 1, 2003, pp. 941-952, XP055025334, ISSN: 0161-5890, DOI:10.1016S0 161-5890(03)00022-1.

Du J et al: "Molecular basis of recognition of human osteopontin by 23C3, a potential therapeutic antibody for treatment of rheumatoid arthritis", Oct. 17, 2008 (Oct. 17, 2008), Journal of Molecular Biology, Academic Press, United Kingdom, pp. 835-842, XP026805063, ISSN: 0022-2836 [retrieved on Jul. 31, 2008].

\* cited by examiner

T4 Fab nucleotide sequences

A. Light chain

GATATTGTTCTCAACCAGTCTCCAGCAATCATGTCTGCATCTCCAGGGGAGAAGGTCACCATGACCTGCAATTCCAGCT
CAAGTGTAAGTTACATGCACTGGTACCAGCATAAGCCAGGATCCTCCCCCCGACTCCTGATTTATGACACATCCAACCT
GGCTTCTGGAGTCCCTGCTCGCTTCAGTGGCAGTGGATCTGGGACCTCTTACTCTCTCACAATCAGCCGAATGGAGGC
TGAAGATGCTGCCACTTATTACTGCCAGCAAGGAGTAGTTACCCGCTCACGTTCGGTGCTGGGACCAAGCTGGAAAT
AACCCGGGCTGATGCTGCACCAACTGTATCCATCTTCCCACCATCCAGTGAGCAGTTAACATCTGGAGGTGCCTCAGTC
GTGTGCTTCTTGAACAACTTCTACCCCAAAGACATCAATGTCAAGTGGAAGATTGATGGCAGTGAACGACAAAATGGC
GTCCTGAACAGTTGGACTGATCAGGACAGCAAAGACAGCACCTACAGCATGAGCAGCACCCTCACGCTCACCAAGGA
CGAGTATGAACGACATAACAGCTATACCTGTGAGGCCACTCACAAGACATCAACTTCACCCATTGTCAAGAGCTTCAA
CAGGAATGAGTGT (SEQ ID NO: 1)

OR

GATATTGTTCTCAACCAGTCTCCAGCAATCATGTCTGCATCTCCAGGGGAGAAGGTCACCATGACCTGCAATTCCAGCT
CAAGTGTAAGTTACATGCACTGGTACCAGCATAAGCCAGGATCCTCCCCCCGACTCCTGATTTATGACACATCCAACCT
GGCTTCTGGAGTCCCTGCTCGCTTCAGTGGCAGTGGATCTGGGACCTCTTACTCTCTCACAATCAGCCGAATGGAGGC
TGAAGATGCTGCCACTTATTACTGCCAGCAAGGAGTAGTNNNCCGCTCACGTTCGGTGCTGGGACCAAGCTGGAAA
TAACCCGGGCTGATGCTGCACCAACTGTATCCATCTTCCCACCATCCAGTGAGCAGTTAACATCTGGAGGTGCCTCAGT
CGTGTGCTTCTTGAACAACTTCTACCCCAAAGACATCAATGTCAAGTGGAAGATTGATGGCAGTGAACGACAAAATGG
CGTCCTGAACAGTTGGACTGATCAGGACAGCAAAGACAGCACCTACAGCATGAGCAGCACCCTCACGCTCACCAAGG
ACGAGTATGAACGACATAACAGCTATACCTGTGAGGCCACTCACAAGACATCAACTTCACCCATTGTCAAGAGCTTCA
ACAGGAATGAGTGT (SEQ ID NO: 7)

B. Heavy chain

GAAGTGAAGCTTGAGGAGTCTGGGGGAGGCTTAGTGAAACTTGGAGGGTCCCTGAAACTCTCCTGTGCAGCCTCTGG
ATTCACTTTCAGTAGCTATTACATGTCTTGGGTTCGCCAGACTCCAGAGAAGAGGCTGGAGTTGGTCGCAGCCATTAA
TAGTAATGGTGGTAGCACCTACTATCCAGACACTGTGAAGGGCCGATTCACCATCTCCAGAGACAATGCCAAGAACAC
CCTGTACCTGCAAATGAGCAGTCTGAAGTCTGAGGACACAGCCTTGTATTACTGTGCAAGAGGGGATTACTACGGTA
GTAGCTTATATTACTATGCTATGGACTACTGGGGTCAAGGAACCTCAGTCACCGTCTCCTCAGCCAAAACGACACCCCC
ATCTGTCTATCCACTGGCCCCTGGATCTGCTGCCCAAACTAACTCCATGGTGACCCTGGGATGCCTGGTCAAGGGCTAT
TTCCCTGAGCCAGTGACAGTGACCTGGAACTCTGGATCCCTGTCCAGCGGTGTGCACACCTTCCCAGCTGTCCTGCAGT
CTGACCTCTACACTCTGAGCAGCTCAGTGACTGTCCCCTCCAGCACCTGGCCCAGCGAGACCGTCACCTGCAACGTTGC
CCACCCGGCCAGCAGCACCAAGGTGGACAAGAAAATTGTGCCCAGGGATTGT (SEQ ID NO:2)

OR

GAAGTGAAGCTTGAGGAGTCTGGGGGAGGCTTAGTGAAACTTGGAGGGTCCCTGAAACTCTCCTGTGCAGCCTCTGG
ATTCACTTTCAGTAGCTATNNNATGTCTTGGGTTCGCCAGACTCCAGAGAAGAGGCTGGAGTTGGTCGCAGCCATTAA
TAGTAATGGTGGTAGCACCNNNTATCCAGACACTGTGAAGGGCCGATTCACCATCTCCAGAGACAATGCCAAGAACA
CCCTGTACCTGCAAATGAGCAGTCTGAAGTCTGAGGACACAGCCTTGTATTACTGTGCAAGAGGGGATTACTACGGTA
GTAGCTTANNNTACNNNGCTATGGACTACTGGGGTCAAGGAACCTCAGTCACCGTCTCCTCAGCCAAAACGACACCC
CCATCTGTCTATCCACTGGCCCCTGGATCTGCTGCCCAAACTAACTCCATGGTGACCCTGGGATGCCTGGTCAAGGGCT
ATTTCCCTGAGCCAGTGACAGTGACCTGGAACTCTGGATCCCTGTCCAGCGGTGTGCACACCTTCCCAGCTGTCCTGCA
GTCTGACCTCTACACTCTGAGCAGCTCAGTGACTGTCCCCTCCAGCACCTGGCCCAGCGAGACCGTCACCTGCAACGTT
GCCCACCCGGCCAGCAGCACCAAGGTGGACAAGAAAATTGTGCCCAGGGATTGTGCGGCCGCACATCATCATCATCA
TCAT (SEQ ID NO: 8)

Figures 1A and B.

T4 Fab amino acid sequences

A. Light chain

DIVLNQSPAIMSASPGEKVTMTCNSSSSVSYMHWYQHKPGSSPRLLIYDTSNLASGVPARFSGSGSGTSYSLTISRMEAED
AATYYCQQRSSYPLTFGAGTKLEITRADAAPTVSIFPPSSEQLTSGGASVVCFLNNFYPKDINVKWKIDGSERQNGVLNSWT
DQDSKDSTYSMSSTLTLTKDEYERHNSYTCEATHKTSTSPIVKSFNRNEC (SEQ ID NO:3)

OR

DIVLNQSPAIMSASPGEKVTMTCNSSSSVSYMHWYQHKPGSSPRLLIYDTSNLASGVPARFSGSGSGTSYSLTISRMEAED
AATYYCQQRSSXPLTFGAGTKLEITRADAAPTVSIFPPSSEQLTSGGASVVCFLNNFYPKDINVKWKIDGSERQNGVLNSWT
DQDSKDSTYSMSSTLTLTKDEYERHNSYTCEATHKTSTSPIVKSFNRNEC (SEQ ID NO:5)

B. Heavy chain

EVKLEESGGGLVKLGGSLKLSCAASGFTFSSYYMSWVRQTPEKRLELVAAINSNGGSTYYPDTVKGRFTISRDNAKNTLYLQ
MSSLKSEDTALYYCARGDYYGSSLYYYAMDYWGQGTSVTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRDC (SEQ ID NO:4)

OR

EVKLEESGGGLVKLGGSLKLSCAASGFTFSSYXMSWVRQTPEKRLELVAAINSNGGSTXYPDTVKGRFTISRDNAKNTLYLQ
MSSLKSEDTALYYCARGDYYGSSLXYXAMDXWGQGTSVTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRDC (SEQ ID NO:6)

Figures 2A and B.

A. Light chain

Figure 3A.

B. Heavy chain

LOD = 84 pM L-Thyroxine (Calculated: Blank (0 nM T4) - 3x Blank StDev)
LOQ = 314 pM L-Thyroxine (Calculated: Blank (0 nM T4) - 10x Blank StDev)
IC50 = 540 pM L-Thyroxine (Calculated: $B/B_0$ = 0.5)
High resolution image:

LOD = 7.6 nM TIBPA (Calculated: Blank (0 nM TIBPA) - 3x Blank StDev)
LOQ = 31 nM TIBPA (Calculated: Blank (0 nM TIBPA) - 10x Blank StDev)
IC50 = 54 nM TIBPA (Calculated: $B/B_0 = 0.5$)
High resolution image:

LOD = 3.7 nM TBBPA (Calculated: Blank (0 nM TBBPA) - 3x Blank StDev)
LOQ = 16.6 nM TBBPA (Calculated: Blank (0 nM TBBPA) - 10x Blank StDev)
IC50 = 74 nM TBBPA (Calculated: $B/B_0 = 0.5$)
High resolution image:

LOD = 39 nM TCBPA (Calculated: Blank (0 nM TCBPA) - 3x Blank StDev)
LOQ = 169 nM TCBPA (Calculated: Blank (0 nM TCBPA) - 10x Blank StDev)
IC50 = 544 nM TCBPA (Calculated: $B/B_0$ = 0.5)
High resolution image:

LOD = - nM BPA (Calculated: Blank (0 nM BPA) - 3x Blank StDev)
LOQ = - nM BPA (Calculated: Blank (0 nM BPA) - 10x Blank StDev)
IC50 = - nM BPA (Calculated: $B/B_0$ = 0.5)
High resolution image:

| Ligand atom | Fab chain | Amino acid residue | Atom | vdw [Å] | hydrogen bond [Å] | Ligand atom | Fab chain | Amino acid residue | Atom | vdw [Å] | hydrogen bond [Å] |
|---|---|---|---|---|---|---|---|---|---|---|---|
| T4 | | | | | | TIBPA | | | | | |
| I5' | H | Y33 | CD1 | 3.9 | | I4' | H | Y33 | CD1 | 4.0 | |
| | | | CE1 | 3.7 | | | | | CE1 | 4.0 | |
| | | | CD2 | 3.8 | | | | | | | |
| | | | CE2 | 3.8 | | | | | | | |
| | | | CG | 3.9 | | | | | | | |
| | | | CZ | 3.7 | | | | | | | |
| | H | Y107 | CG | 3.6 | | | H | Y107 | CG | 3.6 | |
| | | | CD2 | 3.3 | | | | | CD2 | 3.5 | |
| | | | CE2 | 3.8 | | | | | CE2 | 3.9 | |
| | | | CB | 3.9 | | | | | CB | 4.0 | |
| | H | Y109 | CE1 | 3.7 | | | H | Y109 | CE1 | 3.8 | |
| | | | CZ | 3.9 | | | | | | | |
| I3' | H | M111 | CE | 3.6 | | I3' | H | M111 | SD | 3.7 | |
| | | | SD | 3.7 | | | | | | | |
| O4' | H | D100 | OD2 | | 2.3 | O4' | H | D100 | OD2 | | 2.7 |
| | | | N | | 3.5 | | | | N | | 3.1 |
| C2' | H | A50 | CB | 3.5 | | | | | | | |
| C3' | H | Y109 | CD1 | 4.0 | | | | | | | |
| C4' | H | Y109 | CE1 | 4.0 | | | | | | | |
| | | | CD1 | 3.5 | | | | | | | |
| C5' | H | Y109 | CE1 | 3.5 | | C5' | H | Y109 | CE1 | 3.9 | |
| | | | CD1 | 3.5 | | | | | CD1 | 3.6 | |
| | H | Y33 | CG | 3.9 | | | | | | | |
| | | | CD1 | 3.5 | | | | | | | |
| | | | CE1 | 4.0 | | | | | | | |
| C6' | H | Y109 | CE1 | 3.6 | | C6' | H | Y109 | CE1 | 3.7 | |
| | | | CD1 | 3.8 | | | | | CD1 | 3.5 | |
| | | Y33 | CE1 | 3.8 | | | | | | | |
| | | | CD1 | 3.5 | | | | | | | |
| O4 | H | A58 | CB | 2.8 | | | | | | | |
| | | | | | | C8 | L | Y93 | CG | 3.9 | |
| | | | | | | | | | CD1 | 3.5 | |
| | | | | | | | | | CE1 | 3.3 | |
| | | | | | | | | | CZ | 3.5 | |
| | | | | | | C9 | H | Y59 | CD2 | 3.8 | |
| | | | | | | | | | CG | 3.8 | |
| | | | | | | | H | L47 | CD2 | 3.9 | |
| I5 | H | N52 | N | 3.8 | | I2 | H | N52 | N | 3.7 | |
| | | S57 | O | 4.0 | | | | S57 | O | 3.3 | |
| I3 | L | L95 | CG | 3.8 | | | | | | | |
| | | | CD2 | 4.0 | | | | | | | |
| | L | Y93 | CD1 | 3.7 | | | | | | | |
| | | | CE1 | 3.9 | | | | | | | |
| C1 | H | Y59 | CB | 3.9 | | C1 | H | Y59 | CB | 4.0 | |
| C2 | H | Y59 | CD1 | 3.9 | | C2 | H | Y59 | CD1 | 4.0 | |
| | | | CG | 3.9 | | | | | | | |
| | | | CB | 3.9 | | | | | | | |
| | L | Y93 | CE2 | 3.7 | | | | | | | |
| | | | CD2 | 3.8 | | | | | | | |
| C3 | H | Y59 | CB | 3.6 | | | | | | | |
| | | | CG | 3.8 | | | | | | | |
| C4 | H | Y59 | CB | 3.4 | | | | | | | |
| C5 | H | Y59 | CB | 3.5 | | | | | | | |
| C6 | H | Y59 | CB | 3.7 | | | | | | | |
| C7 | L | Y93 | CE2 | 3.7 | | | | | | | |

Figure 10A.

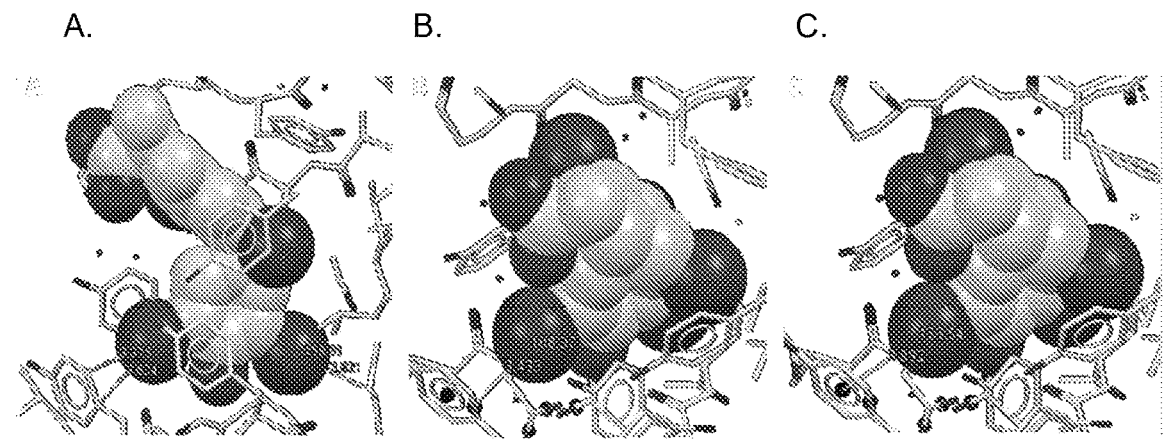
Figures 10B_1.
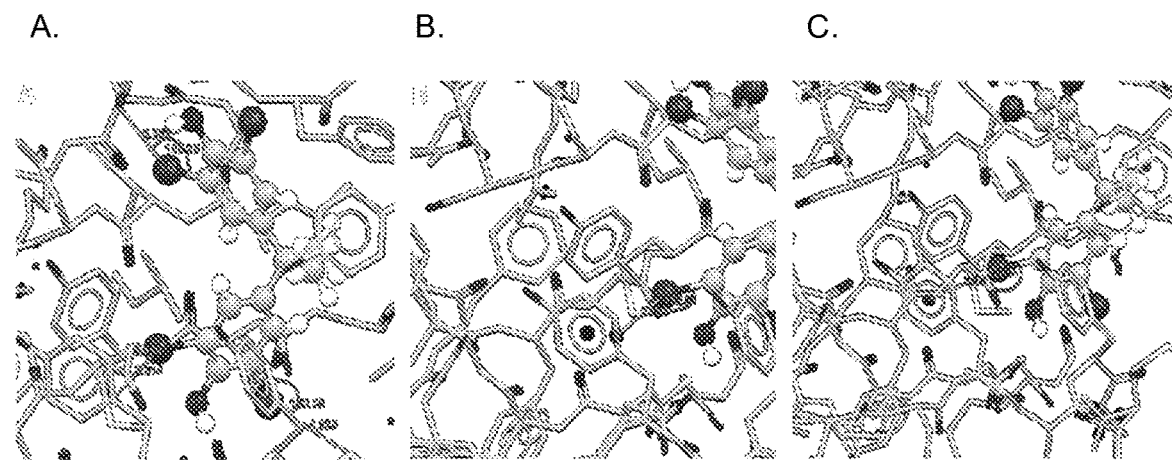
Figures 10B_2.
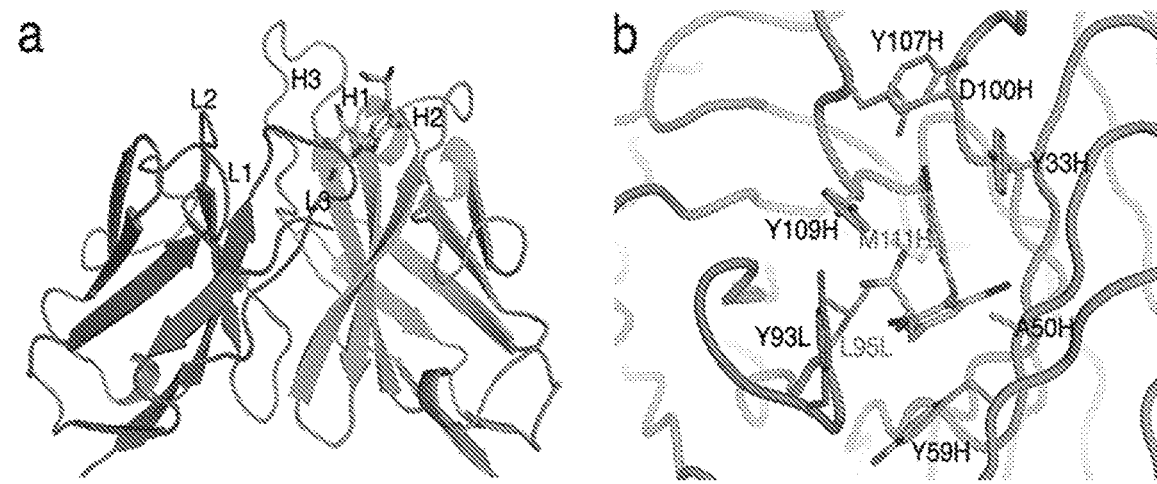
Figures 11A and B.

SEQUENCE LISTING

<160> NUMBER OF SEQ ID NOS: 8

<210> SEQ ID NO 1
<211> LENGTH: 639
<212> TYPE: DNA
<213> ORGANISM: Artificial Sequence
<220> FEATURE:
<223> OTHER INFORMATION: T4 Fab light chain nucleotide sequence

<400> SEQUENCE: 1

```
gatattgttc tcaaccagtc tccagcaatc atgtctgcat ctccagggga gaaggtcacc    60
atgacctgca attccagctc aagtgtaagt tacatgcact ggtaccagca taagccagga   120
tcctcccccc gactcctgat ttatgacaca tccaacctgg cttctggagt ccctgctcgc   180
ttcagtggca gtggatctgg gacctcttac tctctcacaa tcagccgaat ggaggctgaa   240
gatgctgcca cttattactg ccagcaaagg agtagttacc cgctcacgtt cggtgctggg   300
accaagctgg aaataacccg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgctc   540
accaaggacg agtatgaacg acataacagc tatacctgtg aggccactca caagacatca   600
acttcaccca ttgtcaagag cttcaacagg aatgagtgt                          639
```

<210> SEQ ID NO 2
<211> LENGTH: 678
<212> TYPE: DNA
<213> ORGANISM: Artificial Sequence
<220> FEATURE:
<223> OTHER INFORMATION: T4 Fab heavy chain nucleotide sequence

<400> SEQUENCE: 2

```
gaagtgaagc ttgaggagtc tgggggaggc ttagtgaaac ttggagggtc cctgaaactc    60
tcctgtgcag cctctggatt cactttcagt agctattaca tgtcttgggt tcgccagact   120
ccagagaaga ggctggagtt ggtcgcagcc attaatagta atggtggtag cacctactat   180
ccagacactg tgaagggccg attcaccatc tccagagaca atgccaagaa caccctgtac   240
ctgcaaatga gcagtctgaa gtctgaggac acagccttgt attactgtgc aagaggggat   300
tactacggta gtagcttata ttactatgct atggactact ggggtcaagg aacctcagtc   360
accgtctcct cagccaaaac gacaccccca tctgtctatc cactggcccc tggatctgct   420
gcccaaacta actccatggt gaccctggga tgcctggtca agggctattt ccctgagcca   480
gtgacagtga cctggaactc tggatccctg tccagcggtg tgcacacctt cccagctgtc   540
ctgcagtctg acctctacac tctgagcagc tcagtgactg tcccctccag cacctggccc   600
agcgagaccg tcacctgcaa cgttgcccac ccggccagca gcaccaaggt ggacaagaaa   660
attgtgccca gggattgt                                                  678
```

<210> SEQ ID NO 3
<211> LENGTH: 213
<212> TYPE: PRT
<213> ORGANISM: Artificial Sequence
<220> FEATURE:
<223> OTHER INFORMATION: T4 Fab light chain amino acid sequence

<400> SEQUENCE: 3

```
Asp Ile Val Leu Asn Gln Ser Pro Ala Ile Met Ser Ala Ser Pro Gly
  1               5                  10                  15

Glu Lys Val Thr Met Thr Cys Asn Ser Ser Ser Val Ser Tyr Met
             20                  25                  30

His Trp Tyr Gln His Lys Pro Gly Ser Ser Pro Arg Leu Leu Ile Tyr
             35                  40                  45

Asp Thr Ser Asn Leu Ala Ser Gly Val Pro Ala Arg Phe Ser Gly Ser
         50                  55                  60
```

```
Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Leu Thr
                 85                  90                  95

Phe Gly Ala Gly Thr Lys Leu Glu Ile Thr Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 4
<211> LENGTH: 226
<212> TYPE: PRT
<213> ORGANISM: Artificial Sequence
<220> FEATURE:
<223> OTHER INFORMATION: T4 Fab heavy chain amino acid sequence

<400> SEQUENCE: 4

```
Glu Val Lys Leu Glu Glu Ser Gly Gly Gly Leu Val Lys Leu Gly Gly
 1               5                  10                  15

Ser Leu Lys Leu Ser Cys Ala Ala Ser Gly Phe Thr Phe Ser Ser Tyr
             20                  25                  30

Tyr Met Ser Trp Val Arg Gln Thr Pro Glu Lys Arg Leu Glu Leu Val
         35                  40                  45

Ala Ala Ile Asn Ser Asn Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Leu Tyr Tyr Cys
             85                  90                  95

Ala Arg Gly Asp Tyr Tyr Gly Ser Ser Leu Tyr Tyr Ala Met Asp
         100                 105                 110

Tyr Trp Gly Gln Gly Thr Ser Val Thr Val Ser Ser Ala Lys Thr Thr
         115                 120                 125

Pro Pro Ser Val Tyr Pro Leu Ala Pro Gly Ser Ala Ala Gln Thr Asn
    130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
        195                 200                 205
```

```
Ala His Pro Ala Ser Ser Thr Lys Val Asp Lys Lys Ile Val Pro Arg
    210                 215                 220

Asp Cys
225
```

<210> SEQ ID NO 5
<211> LENGTH: 213
<212> TYPE: PRT
<213> ORGANISM: Artificial Sequence
<220> FEATURE:
<223> OTHER INFORMATION: T4 Fab light chain amino acid sequence
<220> FEATURE:
<221> NAME/KEY: misc_feature
<222> LOCATION: (93)..(93)
<223> OTHER INFORMATION: Xaa is Tyr or Phe

<400> SEQUENCE: 5

```
Asp Ile Val Leu Asn Gln Ser Pro Ala Ile Met Ser Ala Ser Pro Gly
1               5                   10                  15

Glu Lys Val Thr Met Thr Cys Asn Ser Ser Ser Val Ser Tyr Met
            20                  25                  30

His Trp Tyr Gln His Lys Pro Gly Ser Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Xaa Pro Leu Thr
                85                  90                  95

Phe Gly Ala Gly Thr Lys Leu Glu Ile Thr Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 6
<211> LENGTH: 226
<212> TYPE: PRT
<213> ORGANISM: Artificial Sequence
<220> FEATURE:
<223> OTHER INFORMATION: T4 Fab heavy chain amino acid sequence
<220> FEATURE:
<221> NAME/KEY: misc_feature
<222> LOCATION: (33)..(33)
<223> OTHER INFORMATION: Xaa is Tyr or Phe
<220> FEATURE:
<221> NAME/KEY: misc_feature
<222> LOCATION: (59)..(59)
<223> OTHER INFORMATION: Xaa is Tyr or Phe
<220> FEATURE:
<221> NAME/KEY: misc_feature
<222> LOCATION: (107)..(107)
<223> OTHER INFORMATION: Xaa is Tyr or Phe
<220> FEATURE:
<221> NAME/KEY: misc_feature
<222> LOCATION: (109)..(109)
<223> OTHER INFORMATION: Xaa is Tyr or Phe
<220> FEATURE:
<221> NAME/KEY: misc_feature
<222> LOCATION: (113)..(113)
<223> OTHER INFORMATION: Xaa is Tyr or Phe

<400> SEQUENCE: 6

```
Glu Val Lys Leu Glu Glu Ser Gly Gly Gly Leu Val Lys Leu Gly Gly
1               5                   10                  15
Ser Leu Lys Leu Ser Cys Ala Ala Ser Gly Phe Thr Phe Ser Ser Tyr
            20                  25                  30
Xaa Met Ser Trp Val Arg Gln Thr Pro Glu Lys Arg Leu Glu Leu Val
        35                  40                  45
Ala Ala Ile Asn Ser Asn Gly Gly Ser Thr Xaa Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Leu Tyr Tyr Cys
                85                  90                  95
Ala Arg Gly Asp Tyr Tyr Gly Ser Ser Leu Xaa Tyr Xaa Ala Met Asp
            100                 105                 110
Xaa Trp Gly Gln Gly Thr Ser Val Thr Val Ser Ser Ala Lys Thr Thr
        115                 120                 125
Pro Pro Ser Val Tyr Pro Leu Ala Pro Gly Ser Ala Ala Gln Thr Asn
    130                 135                 140
Ser Met Val Thr Leu Gly Cys Leu Val Lys Gly Tyr Phe Pro Glu Pro
145                 150                 155                 160
Val Thr Val Thr Trp Asn Ser Gly Ser Leu Ser Ser Gly Val His Thr
                165                 170                 175
Phe Pro Ala Val Leu Gln Ser Asp Leu Tyr Thr Leu Ser Ser Ser Val
            180                 185                 190
Thr Val Pro Ser Ser Thr Trp Pro Ser Glu Thr Val Thr Cys Asn Val
        195                 200                 205
Ala His Pro Ala Ser Ser Thr Lys Val Asp Lys Lys Ile Val Pro Arg
    210                 215                 220
Asp Cys
225
```

<210> SEQ ID NO 7
<211> LENGTH: 639
<212> TYPE: DNA
<213> ORGANISM: Artificial Sequence
<220> FEATURE:
<223> OTHER INFORMATION: T4 Fab light chain nucleotide sequence
<220> FEATURE:
<221> NAME/KEY: misc_feature
<222> LOCATION: (277)..(279)
<223> OTHER INFORMATION: n is a, c, g, or t

<400> SEQUENCE: 7

```
gatattgttc tcaaccagtc tccagcaatc atgtctgcat ctccagggga gaaggtcacc    60
atgacctgca attccagctc aagtgtaagt tacatgcact ggtaccagca taagccagga   120
tcctccccccc gactcctgat ttatgacaca tccaacctgg cttctggagt ccctgctcgc   180
ttcagtggca gtggatctgg gacctcttac tctctcacaa tcagccgaat ggaggctgaa   240
```

```
gatgctgcca cttattactg ccagcaaagg agtagtnnnc cgctcacgtt cggtgctggg    300
accaagctgg aaataacccg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgctc    540
accaaggacg agtatgaacg acataacagc tatacctgtg aggccactca caagacatca    600
acttcaccca ttgtcaagag cttcaacagg aatgagtgt                          639

<210> SEQ ID NO 8
<211> LENGTH: 705
<212> TYPE: DNA
<213> ORGANISM: Artificial Sequence
<220> FEATURE:
<223> OTHER INFORMATION: T4 Fab heavy chain nucleotide sequence
<220> FEATURE:
<221> NAME/KEY: misc_feature
<222> LOCATION: (97)..(99)
<223> OTHER INFORMATION: n is a, c, g, or t
<220> FEATURE:
<221> NAME/KEY: misc_feature
<222> LOCATION: (175)..(177)
<223> OTHER INFORMATION: n is a, c, g, or t
<220> FEATURE:
<221> NAME/KEY: misc_feature
<222> LOCATION: (319)..(321)
<223> OTHER INFORMATION: n is a, c, g, or t
<220> FEATURE:
<221> NAME/KEY: misc_feature
<222> LOCATION: (325)..(327)
<223> OTHER INFORMATION: n is a, c, g, or t

<400> SEQUENCE: 8
gaagtgaagc ttgaggagtc tggggggaggc ttagtgaaac ttggagggtc cctgaaactc     60
tcctgtgcag cctctggatt cactttcagt agctatnnna tgtcttgggt tcgccagact    120
ccagagaaga ggctggagtt ggtcgcagcc attaatagta atggtggtag caccnnntat    180
ccagacactg tgaagggccg attcaccatc tccagagaca tgccaagaa caccctgtac     240 ctgcaaatga gcagtctgaa gtctgaggac acagccttgt attactgtgc aagaggggat    300
tactacggta gtagcttann ntacnnngct atggactact ggggtcaagg aacctcagtc    360
accgtctcct cagccaaaac gacaccccca tctgtctatc cactggcccc tggatctgct    420
gcccaaacta actccatggt gaccctggga tgcctggtca agggctattt ccctgagcca    480
gtgacagtga cctggaactc tggatccctg tccagcggtg tgcacacctt cccagctgtc    540
ctgcagtctg acctctacac tctgagcagc tcagtgactg tcccctccag cacctggccc    600
agcgagaccg tcacctgcaa cgttgcccac ccggccagca gcaccaaggt ggacaagaaa    660
attgtgccca gggattgtgc ggccgcacat catcatcatc atcat                   705
```

ANTI-THYROID HORMONE (T4) RECOMBINANT ANTIBODY OR ANTIGEN BINDING FRAGMENT

PRIORITY

This application is a U.S. national application of the international application number PCT/FI2019/050408 filed on May 28, 2019 and claiming priority of FI application number 20185486 filed on May 29, 2018, the contents of all of which are incorporated herein by reference.

REFERENCE TO A SEQUENCE LISTING

This application contains a sequence listing as an ASCII text file identified by the file name "Sequence_listing_PI100841.txt" created on Nov. 23, 2020 and having a size of 12.9 kb, which is hereby incorporated herein by reference.

FIELD OF THE INVENTION

The present invention relates to the fields of antibodies, antigen binding fragments and immunodiagnostics. Specifically, the invention relates to a recombinant antibody or antigen binding fragment for binding thyroid hormone T4 (thyroxine) and halogenated bisphenol A. Also, the present invention relates to an isolated nucleic acid molecule comprising a nucleotide sequence that encodes the recombinant antibody or antigen binding fragment of the present invention, as well as an expression vector and host cell comprising the nucleic acid molecule of the present invention. Still, the present invention relates to a method of producing a recombinant antibody or antigen binding fragment for binding T4 thyroid hormone and halogenated bisphenol A, a test kit and an immunoassay comprising the recombinant antibody or antigen binding fragment of the present invention, and a method for determining T4 thyroid hormone and/or halogenated bisphenol A levels in a sample of a subject. Still further, the present invention relates to a method of treating a sample, e.g. an immunoaffinity-based sample preparation method for enrichment of the halogenated bisphenol A from a sample.

BACKGROUND

Thyroid hormones have an important role in differentiation, growth and metabolism. The thyroid hormones, triiodothyronine (T3) and thyroxine (T4) are produced by the thyroid gland. The precursors for T4 are tyrosine amino acids of the thyroglobulin expressed in thyroid gland. Tyrosine amino acids are combined with iodine, two iodinated tyrosines are conjugated and subsequently cleaved from the thyroglobulin. T4 is further converted to T3 by deiodinase enzymes within the target cells. The difference between T4- and T3-hormones is only one iodine atom.

T4 is the dominant thyroid hormone in serum with concentration ca 40 fold higher than T3 (90 nM and 2 nM, respectively). Only 0.03% of the total T4 in serum (10-25 pM) and 0.3% of T3 (4.0-8.0 pM) is in an unbound form which enters the cells and has the biological activity (Yen, P. M. Physiological Reviews (2001) 81:1097-1142).

At the moment, the commonly used test for analyzing T4 from serum is a radioimmunoassay (RIA). The determination of the free T4 is an important tool for screening of the potential thyroid dysfunction. When unusual values are obtained then more thorough diagnostics to clarify the cause of thyroid gland dysfunction is performed (free and bound T4, T3, TSH and autoantibodies). In some disorders increasing amounts of T3 are produced while T4 levels are normal. Therefore, it is important to have multiplexed diagnostics to have a comprehensive picture of thyroid gland function.

T4 has one iodine more than T3. This minor difference between the most important thyroid hormones makes the specific antibody discovery for either T3 or T4 very challenging. In addition, both thyroid hormones T3 and T4 are relatively small and hydrophobic.

Several commercial antibody products, either poly- or monoclonal, are available for thyroid hormones. Also, several patent applications relate to thyroid hormone antibodies. E.g. JP2010178649 (A) describes an anti-thyroxine antibody comprising a specific heavy chain variable region ($V_H$) and a specific light chain variable region ($V_L$). Islam et al (2011) describes an antibody for T4 which in recombinant Fab-format was selected using a phage display technology and used for the one-step open immunoassay (Islam K N et al. Analytical Chemistry (2011) 83: 1008-1014).

Still, antibodies or antigen binding fragments having especially high affinity for T4 are needed for determination of thyroid hormone T4 in a biological sample.

SUMMARY OF THE INVENTION

The present invention concerns a novel reagent for rapid and reliable detection of T4 thyroid hormone. Also, the present invention concerns a novel reagent for rapid and reliable detection of halogenated bisphenol A.

The present invention reveals surprising binding properties of an antibody or antigen binding fragment capable of binding thyroid hormones and halogenated bisphenol A. Indeed, the present invention relates to a recombinant antibody or antigen binding fragment capable of binding thyroid hormone T4 with high affinity and capable of halogen dependent binding to halogenated bisphenol A.

One surprising advantage of the present invention includes that observed levels of halogenated bisphenol A in humans do not disturb the immunoassay when high affinity anti-T4 antibody is used. However, the cross reactivity of the T4 thyroid hormone binding antibody or antigen binding fragment of the present invention for the halogenated bisphenol A makes it possible to use the same antibody for the measurement and/or sample preparation of halogenated bisphenol A from e.g. biological, environmental or food samples. Cross-reactivity also provides efficient tools for evaluating the endocrine disruptor potential of organic molecules having effect on the thyroid hormone system.

The present invention relates to a recombinant antibody or antigen binding fragment (e.g. isolated antibody or antigen binding fragment) for binding T4 thyroid hormone and halogenated bisphenol A.

Also, the present invention relates to an isolated (recombinant) nucleic acid molecule comprising a nucleotide sequence that encodes the recombinant antibody or antigen binding fragment of the present invention.

Also, the present invention relates to an expression vector comprising the nucleic acid molecule of the present invention.

Still, the present invention relates to a host cell comprising the nucleic acid molecule or the expression vector of the present invention.

Furthermore, the present invention relates to a method of producing a recombinant antibody or antigen binding fragment for binding T4 thyroid hormone and halogenated bisphenol A (e.g. triiodobisphenol or tetrahalobisphenol A)

of the present invention, wherein the method comprises introducing an expression vector of the present invention into a host cell and growing the cell under conditions permitting production of the antibody or antigen binding fragment.

Furthermore, the present invention relates to a test kit comprising the recombinant antibody or antigen binding fragment of the present invention. Also, use of said test kit for detecting T4 thyroid hormone and/or halogenated bisphenol A in a sample is within the scope of the present invention. Furthermore, use of a kit comprising the recombinant antibody or antigen binding fragment of the present invention for treating a sample is within the scope of the present invention.

Still furthermore, the present invention relates to a method for determining T4 thyroid hormone and/or halogenated bisphenol A concentration(s) in a sample, wherein the method comprises allowing the recombinant antibody or antigen binding fragment of the present invention to contact with a sample (such as a biological, environmental or food sample, or a sample of a subject) and thereafter determining the concentration of T4 thyroid hormone and/or halogenated bisphenol A, respectively, in said sample.

Still furthermore, the present invention relates to a method for treating (e.g. pretreating) a sample, wherein the method comprises allowing the recombinant antibody or antigen binding fragment of the present invention to contact with a sample (such as a biological, environmental, material or food sample, or a sample of a subject).

And still, the present invention relates to an immunoassay comprising the recombinant antibody or antigen binding fragment of the present invention.

And still furthermore, the present invention relates to use of the recombinant antibody or antigen binding fragment or the immunoassay of the present invention for screening endocrine disruptor potential (e.g. endocrine disruptor potential related to the thyroid axis) present in a sample.

Other objects, details and advantages of the invention will become apparent from the following drawings, detailed description and examples.

BRIEF DESCRIPTION OF THE DRAWINGS

FIG. 1a shows the nucleotide sequence of the T4 Fab light chain (SEQ ID NO: 1 or SEQ ID NO: 7 (in SEQ ID NO: 7 each DNA codon NNN is independently selected from the group consisting of DNA codons TAO, TAT, TTT and TTC)).

FIG. 1b shows the nucleotide sequence of the T4 Fab heavy chain (SEQ ID NO: 2 or SEQ ID NO: 8 (in SEQ ID NO: 8 each DNA codon NNN is independently selected from the group consisting of DNA codons TAO, TAT, TTT and TTC)).

FIG. 2a shows the amino acid sequence of the T4 Fab light chain (SEQ ID NO: 3 or SEQ ID NO: 5 (in SEQ ID NO: 5 each X is independently either Y (tyrosine) or F (phenylalanine))). CDR regions are marked in bold. The three complementary regions LCDR1 (amino acids 24-33 of SEQ ID NO: 3 or SEQ ID NO: 5, according to Kabat amino acids 24-34), LCDR2 (amino acids 49-55 of SEQ ID NO: 3 or SEQ ID NO: 5, according to Kabat amino acids 50-56) and LCDR3 (amino acids 88-96 of SEQ ID NO: 3 or SEQ ID NO: 5, according to Kabat 89-97) of each immunoglobulin chain are shown.

FIG. 2b shows the amino acid sequence of the T4 Fab heavy chain (SEQ ID NO: 4 or SEQ ID NO: 6 (in SEQ ID NO: 6 each X is independently either Y (tyrosine) or F (phenylalanine)). CDR regions are marked in bold. The three complementary regions HCDR1 (amino acids 31-35 of SEQ ID NO: 4 or SEQ ID NO: 6, according to Kabat amino acids 31-35), HCDR2 (amino acids 50-66 of SEQ ID NO: 4 or SEQ ID NO: 6, according to Kabat amino acids 50-65) and HCDR3 (amino acids 99-113 of SEQ ID NO: 4 or SEQ ID NO: 6, according to Kabat amino acids 95-102) of each immunoglobulin chain are shown.

FIG. 3a shows the amino acid sequence of the T4 Fab light chain (according to SEQ ID NO: 3). CDR regions are underlined and amino acids (at least Y93) responsible for T4 binding are identified.

FIG. 10a reveals interatomic distances up to 4.0 Å between the atoms of T4 and TIBPA ligands and anti-T4 Fab.

FIG. 10b reveal interatomic distances responsible for halogen bonding. FIG. 10b_1 shows relevant halogen bonds in the structure of anti-T4 Fab and T4. A) I5' . . . CD2 distance of 3.375 Å and I5' . . . CG distance of 3.624 Å involving residue Y107 of the T4 Fab heavy chain. I3'-SD distance of 3.621 Å and C3'-I3'-SD angle of 158.31° involving residue M111 of the T4 Fab heavy chain; B) I5' . . . CE2-CD2 bond centroid distance of 3.433 Å and C5'-I5' . . . CE2-CD2 bond centroid angle of 166.37° involving residue Y107 of the T4 Fab heavy chain; C) I5' . . . Y107 ring centroid distance of 3.892 Å and C5'-I5' . . . Y107 ring centroid angle of 173.54°. FIG. 10b_2 shows relevant halogen bonds in the structure of anti-T4 Fab and tetraiodobisphenol A. A) I4' . . . CD2 distance of 3.489 Å and I4' . . . CG distance of 3.614 Å involving residue Y107 of the T4 Fab heavy chain; I3' . . . SD distance of 4.129 Å and C2-I3' . . . SD angle of 153.05° involving residue M111. I2 . . . O distance of 3.257 Å and C15-I2 . . . O angle of 148.38° involving backbone oxygen of residue S57 of the T4 Fab heavy chain; B) I4' . . . CD2-CG bond centroid distance of 3.483 Å and C4-I4' . . . CD2-CG bond centroid angle of 152.91° involving residue Y107 of the T4 Fab heavy chain; C) I4' . . . Y107 ring centroid distance of 3.808 Å and C4-I4' . . . Y107 ring centroid angle of 169.54°.

FIG. 11a shows the variable domains of T4 Fab fragment from the crystal structure. L-chain is in dark grey, H-chain in light grey. Bound T4 molecule is shown as a stick model. Six CDR loops of Fab fragment are labelled (L1, L2, L3, H1, H2, H3).

FIG. 11b shows the binding cleft of T4 Fab fragment with the bound T4 molecule. Residues which participate in T4 binding are shown as stick models and labelled.

SEQUENCE LISTING

Figure 3B:
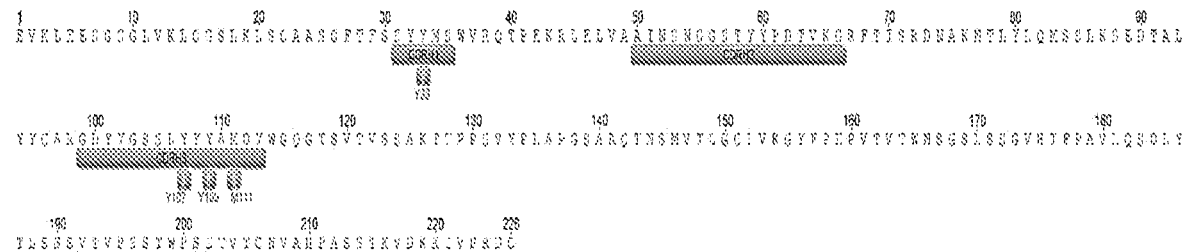
FIG. 3b shows the amino acid sequence of the T4 Fab heavy chain (according to SEQ ID NO: 4). CDR regions are underlined and amino acids (at least Y33, Y107, Y109 and/or M111, or any combination thereof) responsible for T4 binding are identified.

Sequences or partial sequences of anti-T4 thyroid hormone antibody (e.g. T4) or antigen binding fragment of the present invention
- SEQ ID NO:1: T4 Fab Light Chain nucleotide sequence
- SEQ ID NO:2: T4 Fab Heavy Chain nucleotide sequence
- SEQ ID NO:3: T4 Fab Light Chain amino acid sequence
- SEQ ID NO:4: T4 Fab Heavy Chain amino acid sequence
- SEQ ID NO:5: T4 Fab Light Chain amino acid sequence (wherein each X is independently Y or F)
- SEQ ID NO:6: T4 Fab Heavy Chain amino acid sequence (wherein each X is independently Y or F)
- SEQ ID NO:7: T4 Fab Light Chain nucleotide sequence (wherein each DNA codon nnn is independently selected from the group consisting of DNA codons TAC, TAT, TTT and TTC)
- SEQ ID NO:8: T4 Fab Heavy Chain nucleotide sequence (wherein each DNA codon nnn is independently selected from the group consisting of DNA codons TAC, TAT, TTT and TTC)

DETAILED DESCRIPTION OF THE INVENTION

In one embodiment of the invention a recombinant antibody or antigen binding fragment of the present invention binds (e.g. specifically) T4 thyroid hormone.

Thyroxine (3,5,3',5'-tetraiodothyronine) or T4 thyroid hormone belongs to the group of thyroid hormones (T4 and T3) and is produced by the follicular cells of the thyroid gland. The effects of T4 in vivo are mediated via T3 when T4 is converted to T3 in target tissues.

T4 is the most commonly measured thyroid hormone for diagnosis of thyroid function. Thyroid function is studied by detecting T4 levels of blood samples. T4 has its primary influence on protein synthesis and oxygen consumption in all tissues but it is also important for growth, development and sexual maturation. Increased levels of T4 have been found e.g. in samples of patients suffering from hyperthyroidism due to Grave's disease or Plummer's disease, or acute or subacute thyroiditis. Low levels of T4 have been associated with congenital hypothyroidism, myxedema, chronic thyroiditis and some chronic genetic abnormalities.

T4 can be measured as free T4, which is an indicator of T4 activities in the body. The free T4 index relates to total T4 multiplied by thyroid hormone uptake, which, in turn, is a measure of the unbound T4-binding globulins. In one embodiment of the invention T4 is measured as free T4 e.g. by utilizing sensors. T4 can also be measured as total T4, which depends on the T4 that is bound to T4-binding globulin. In one embodiment of the invention T4 is measured as total T4 e.g. by utilizing an immunoassay (such as ELISA or RIA) or sensors or any suitable method known to a person skilled in the art.

In one embodiment of the invention a recombinant antibody or antigen binding fragment of the present invention binds (e.g. specifically) halogenated bisphenol A.

Bisphenol A and its halogenated analogues are commonly used industrial chemicals with strong toxicological effects in many organisms. BPA is employed to make certain plastics and epoxy resins. Bisphenol A is an organic synthetic compound with the chemical formula $(CH_3)_2C(C_6H_4OH)_2$ belonging to the group of diphenylmethane derivatives and bisphenols, with two hydroxyphenyl groups. It is a colorless solid that is soluble in organic solvents, but poorly soluble in water.

Bisphenol A has the following formula I:

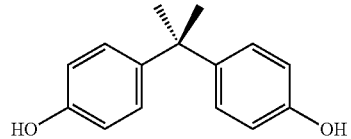

(Formula I)

As used herein "halogenated bisphenol A" refers to bisphenol A, which has been halogenated with 1 or more halogens (e.g. one, two, three, four, five or six halogens, e.g. 1-4 halogen substituents). In a very specific embodiment halogenated bisphenol A is triiodobisphenol A or tetrahalobisphenol A. One or more halogens of the halogenated bisphenol A are independently selected from the group consisting of fluorine (F), chlorine (Cl), bromine (Br) and iodine (I). In a very specific embodiment bisphenol A is halogenated with iodine, bromine, chlorine or a combination thereof. In another very specific embodiment of the invention, halogenated bisphenol A comprises 1, 2, 3 or 4 iodine, bromine or chlorine substituents.

In one embodiment the bisphenol A derivative has the following formula II:

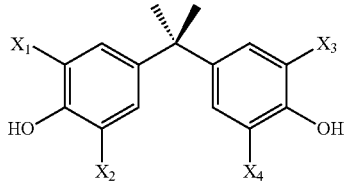

(Formula II)

wherein bisphenol A has been halogenated in one or more positions $X_{1-4}$ with one or more substituents (i.e. one, two, three, or four halogen substituents), wherein each substituent is selected independently from the group consisting of fluorine (F), chlorine (Cl), bromine (Br) and iodine (I).

In one embodiment of the invention, T4 thyroid hormone and halogenated bisphenol A are detected concurrently.

As used herein "an antibody or antigen binding fragment" refers to any antibody or a fragment thereof which is capable to bind T4 thyroid hormone. The term includes e.g. any fragments or single chain antibodies (e.g. Fab, scFv) having the desired biological activities. As an example any complementarity determining regions, heavy chain variable regions, light chain variable regions and any combinations thereof are included within the scope of "antigen binding fragments". As used in this context "a fragment" refers to any part of a polypeptide or protein.

As used herein "antibodies" refer to polypeptides or proteins produced by immune cells or by recombinant techniques in response to antigens. An antibody is an immunoglobulin molecule and it can belong to any of classes IgG, IgM, IgE, IgA or IgD; IgG and IgM being the most frequently used. As used herein "binding polypeptides" refer to polypeptides which bind to antigens of interest. In some embodiments binding polypeptides may inhibit or suppress the function of antigens (polypeptides, proteins, polysaccharides) of interest.

In antibodies variable loops between β-strands, three on each light ($V_L$) and heavy ($V_H$) chain, are responsible for binding to the antigen. These loops are referred to as the complementarity determining regions (CDRs). As used herein, the term "hypervariable region" refers to the amino acid residues of an antibody or fragment thereof which are responsible for antigen binding. The hypervariable region comprises amino acid residues from a CDR (e.g. residues 24-34 (L1), 50-56 (L2) and 89-97 (L3) in the light chain variable domain and 31-35 (H1), 50-65 (H2) and 95-102 (H3) in the heavy chain variable domain according to Kabat et al., (Sequences of Proteins of Immunological Interest, 5th Ed. Public Health Service, National Institutes of Health, Bethesda, Md. (1991)) and/or other amino acid residues from a "hypervariable loop" (framework region). "Framework Region" or "FR" residues are those variable domain residues other than the very specific hypervariable region residues defined by residue numbers in this disclosure. As used herein, the terms "heavy chain variable domain," "$V_H$ domain" and/or "$V_H$" are used interchangeably and reference the hypervariable region (encompassing both the CDR and framework domains) of the heavy chain of an antibody; the terms "light chain variable domain," "$V_L$ domain" and/or "$V_L$" are used interchangeably and reference the hypervariable region (encompassing both the CDR and framework domains) of the heavy chain of an antibody.

At the molecular level, an antigen can be characterized by its ability to bind to an antibody's variable Fab region or antigen binding fragment. As used herein "a ligand" is a molecule that forms a complex e.g. with an anti-T4 antibody Fab or scFv.

"Fv" (variable domain) refers to the variable regions of the immunoglobulin molecule that are responsible for the ligand binding. "A single-chain Fv fragment (scFv)" refers to a fragment comprising the $V_H$ and the $V_L$ domains (variable regions) of the immunoglobulin molecule connected by a linker in a single polypeptide synthesized from a single mRNA molecule.

In one embodiment of the invention the recombinant antibody or antigen binding fragment comprises constant regions, which correspond to human or non-human constant regions. In another embodiment at least part of the variable regions of the recombinant antibody or antigen binding fragment correspond to human or non-human variable regions.

As used herein "a Fab fragment" (fragment antigen-binding) refers to a region of an antibody consisting of the variable and constant domains of an immunoglobulin light chain covalently attached by a disulfide bridge to the variable and first constant domain of an immunoglobulin heavy chain.

In one embodiment of the invention the recombinant antibody or antigen binding fragment comprises amino acids of one or more (e.g. at least two, at least three, at least four, at least five or at least six) complementarity determining regions (CDRs) selected from the group consisting of
  a light chain region 1 comprising amino acids corresponding to amino acids 24-33 of SEQ ID NO:3,
  a light chain region 2 comprising amino acids corresponding to amino acids 49-55 of SEQ ID NO:3,
  a light chain region 3 comprising amino acids corresponding to amino acids 88-96 of SEQ ID NO:3,
  a heavy chain region 1 comprising amino acids corresponding to amino acids 31-35 of SEQ ID NO:4,
  a heavy chain region 2 comprising amino acids corresponding to amino acids 50-66 of SEQ ID NO:4, and
  a heavy chain region 3 comprising amino acids corresponding to amino acids 99-113 of SEQ ID NO:4.

In one embodiment of the invention the recombinant antibody or antigen binding fragment comprises amino acids of one or more (e.g. at least two, at least three, at least four, at least five or at least six) complementarity determining regions (CDRs) selected from the group consisting of
  a light chain region 1 comprising amino acids corresponding to amino acids 24-33 of SEQ ID NO:5,
  a light chain region 2 comprising amino acids corresponding to amino acids 49-55 of SEQ ID NO:5,
  a light chain region 3 comprising amino acids corresponding to amino acids 88-96 of SEQ ID NO:5,
  a heavy chain region 1 comprising amino acids corresponding to amino acids 31-35 of SEQ ID NO:6,
  a heavy chain region 2 comprising amino acids corresponding to amino acids 50-66 of SEQ ID NO:6, and
  a heavy chain region 3 comprising amino acids corresponding to amino acids 99-113 of SEQ ID NO:6.

In one embodiment of the invention the recombinant antibody or antigen binding fragment comprises a heavy chain variable domain amino acid sequence comprising a CDR3 as set forth in amino acids 99-113 of SEQ ID NO:4. In one embodiment of the invention the recombinant antibody or antigen binding fragment comprises a heavy chain variable domain amino acid sequence comprising a CDR3 as set forth in amino acids 99-113 of SEQ ID NO:6.

In one embodiment of the invention the recombinant antibody or antigen binding fragment comprises a heavy chain variable domain amino acid sequence comprising a CDR3 as set forth in amino acids 99-113 of SEQ ID NO:4, and a CDR2 as set forth in amino acids 50-66 of SEQ ID NO:4 or a CDR1 as set forth in amino acids 31-35 of SEQ ID NO:4. In one embodiment of the invention the recombinant antibody or antigen binding fragment comprises a heavy chain variable domain amino acid sequence comprising a CDR3 as set forth in amino acids 99-113 of SEQ ID NO:6, and a CDR2 as set forth in amino acids 50-66 of SEQ ID NO:6 or a CDR1 as set forth in amino acids 31-35 of SEQ ID NO:6.

In one embodiment of the invention the recombinant antibody or antigen binding fragment comprises a heavy chain variable domain amino acid sequence comprising a CDR1 as set forth in amino acids 31-35 of SEQ ID NO:4, a CDR2 as set forth in amino acids 50-66 of SEQ ID NO:4, and a CDR3 as set forth in amino acids 99-113 of SEQ ID NO:4. In one embodiment of the invention the recombinant antibody or antigen binding fragment comprises a heavy chain variable domain amino acid sequence comprising a CDR1 as set forth in amino acids 31-35 of SEQ ID NO:6, a CDR2 as set forth in amino acids 50-66 of SEQ ID NO:6, and a CDR3 as set forth in amino acids 99-113 of SEQ ID NO:6.

In one embodiment of the invention the recombinant antibody or antigen binding fragment comprises
a heavy chain variable domain amino acid sequence comprising a CDR1 as set forth in amino acids 31-35 of SEQ ID NO:4, a CDR2 as set forth in amino acids 50-66 of SEQ ID NO:4, and a CDR3 as set forth in amino acids 99-113 of SEQ ID NO:4; and
a light chain variable domain amino acid sequence comprising a CDR3 as set forth in amino acids 88-96 of SEQ ID NO:3.

In one embodiment of the invention the recombinant antibody or antigen binding fragment comprises
a heavy chain variable domain amino acid sequence comprising a CDR1 as set forth in amino acids 31-35 of SEQ ID NO:6, a CDR2 as set forth in amino acids 50-66 of SEQ ID NO:6, and a CDR3 as set forth in amino acids 99-113 of SEQ ID NO:6; and
a light chain variable domain amino acid sequence comprising a CDR3 as set forth in amino acids 88-96 of SEQ ID NO:5.

In one embodiment of the invention the recombinant antibody or antigen binding fragment comprises
a heavy chain variable domain amino acid sequence comprising a CDR1 as set forth in amino acids 31-35 of SEQ ID NO:4, a CDR2 as set forth in amino acids 50-66 of SEQ ID NO:4, and a CDR3 as set forth in amino acids 99-113 of SEQ ID NO:4; and
a light chain variable domain amino acid sequence comprising a CDR3 as set forth in amino acids 88-96 of SEQ ID NO:3, and a CDR1 as set forth in amino acids 24-33 or a CDR2 as set forth in amino acids 49-55 of SEQ ID NO:3.

In one embodiment of the invention the recombinant antibody or antigen binding fragment comprises
a heavy chain variable domain amino acid sequence comprising a CDR1 as set forth in amino acids 31-35 of SEQ ID NO:6, a CDR2 as set forth in amino acids 50-66 of SEQ ID NO:6, and a CDR3 as set forth in amino acids 99-113 of SEQ ID NO:6; and
a light chain variable domain amino acid sequence comprising a CDR3 as set forth in amino acids 88-96 of SEQ ID NO:5, and a CDR1 as set forth in amino acids 24-33 or a CDR2 as set forth in amino acids 49-55 of SEQ ID NO:5.

In a specific embodiment of the present invention the antibody or antigen binding fragment comprises light chain CDRs 1-3 comprising or consisting of amino acids corresponding to amino acids 24-33, 49-55, and 88-96 of SEQ ID NO:3, respectively, and heavy chain CDRs 1-3 comprising or consisting of amino acids corresponding to amino acids 31-35, 50-66, and 99-113 of SEQ ID NO:4, respectively. In a specific embodiment of the present invention the antibody or antigen binding fragment comprises light chain CDRs 1-3 comprising or consisting of amino acids corresponding to amino acids 24-33, 49-55, and 88-96 of SEQ ID NO:5, respectively, and heavy chain CDRs 1-3 comprising or consisting of amino acids corresponding to amino acids 31-35, 50-66, and 99-113 of SEQ ID NO:6, respectively.

In one embodiment of the invention the recombinant antibody or antigen binding fragment comprises or consists of a light chain comprising or consisting of the amino acid sequence of SEQ ID NO:3 and/or a heavy chain comprising or consisting of the amino acid sequence SEQ ID NO:4. In one embodiment of the invention the recombinant antibody or antigen binding fragment comprises or consists of a light chain comprising or consisting of the amino acid sequence of SEQ ID NO:5 and/or a heavy chain comprising or consisting of the amino acid sequence SEQ ID NO:6.

In one embodiment of the invention the heavy chain variable region ($V_H$) of the recombinant antibody or antigen binding fragment comprises or consists of amino acids 1-124 of SEQ ID NO: 4 and/or the light chain variable region ($V_L$) of the recombinant antibody or antigen binding fragment comprises or consists of amino acids 1-109 of SEQ ID NO: 3. In one embodiment of the invention the heavy chain variable region ($V_H$) of the recombinant antibody or antigen binding fragment comprises or consists of amino acids 1-124 of SEQ ID NO: 6 and/or the light chain variable region ($V_L$) of the recombinant antibody or antigen binding fragment comprises or consists of amino acids 1-109 of SEQ ID NO: 5.

In one embodiment of the invention one or more amino acids of the recombinant antibody or antigen binding fragment corresponding to amino acid residues presented in FIG. 10A and/or FIGS. 3A-B are responsible for binding T4 and/or halogenated bisphenol A. In one embodiment of the invention at least one or more amino acids of the recombinant antibody or antigen binding fragment corresponding to Y93 defined in SEQ ID NO: 3 and/or corresponding to amino acids Y33, Y107, Y109 and M111 defined in SEQ ID NO: 4 are responsible for binding T4 (see e.g. FIGS. 3A and B). In a specific embodiment at least an amino acid of the recombinant antibody or antigen binding fragment corresponding to amino acid Y93 of the light chain defined in SEQ ID NO: 3 and/or at least amino acids of the recombinant antibody or antigen binding fragment corresponding to amino acids Y33, Y107, Y109 and M111 of the heavy chain defined in SEQ ID NO: 4 bind T4. Alternatively or in addition to anyone of the above mentioned Y93, Y33, Y107, Y109 and M111, an amino acid of the recombinant antibody or antigen binding fragment corresponding to e.g. D100, A50, N52, S57, Y59 and/or L47 of the heavy chain defined in SEQ ID NO: 4 and/or L95 of the light chain defined in SEQ ID NO: 3 may be responsible for binding T4 and/or halogenated bisphenol A.

In one embodiment of the invention at least one or more amino acids of the recombinant antibody or antigen binding fragment corresponding to Y93 or F93 defined in SEQ ID NO: 3 or SEQ ID NO: 5, and/or corresponding to amino acids Y33, F33, Y107, F107, Y109, F109 and M111 defined in SEQ ID NO: 4 or SEQ ID NO: 6 are responsible for binding T4 (see e.g. FIG. 10A, FIGS. 2A and B, or FIGS. 3A and B). In a specific embodiment at least an amino acid of the recombinant antibody or antigen binding fragment corresponding to amino acid Y93 or F93 of the light chain defined in SEQ ID NO: 3 or SEQ ID NO: 5, and/or at least amino acids of the recombinant antibody or antigen binding fragment corresponding to amino acids Y33, F33, Y107, F107, Y109, F109 and M111 of the heavy chain defined in SEQ ID NO: 4 or SEQ ID NO: 6 bind T4. Alternatively or in addition to anyone of the above mentioned Y93, F93, Y33, F33, Y107, F107, Y109, F109 and M111, an amino acid of the recombinant antibody or antigen binding fragment corresponding to e.g. D100, A50, N52, S57, Y59, F59 and/or L47 of the heavy chain defined in SEQ ID NO: 4 or SEQ ID NO: 6, and/or L95 of the light chain defined in SEQ ID NO: 3 or SEQ ID NO: 5 may be responsible for binding T4 and/or halogenated bisphenol A.

In one embodiment of the invention one or more amino acids of the recombinant antibody or antigen binding fragment corresponding to one or more amino acid residues presented in FIG. 10A or 10B are responsible for halogen binding. Any tyrosine (Y) mentioned in FIG. 10A may independently be replaced with phenylalanine (F). In one embodiment amino acids of the recombinant antibody or antigen binding fragment responsible for halogen binding are selected from the group consisting of Y33, F33, Y107, F107, Y109, F109, M111, N52 and S57 corresponding to amino acids defined in SEQ ID NO: 4 or SEQ ID NO: 6, and L95 and either Y93 or F93 corresponding to amino acids defined in SEQ ID NO: 3 or SEQ ID NO: 5. In a further embodiment of the invention at least amino acids corresponding to amino acids Y107 or F107 and M111, or corresponding to at least amino acids Y33 or F33, Y107 or F107, Y109 or F109, and M111 of the heavy chain defined in SEQ ID NO: 4 or SEQ ID NO: 6 are responsible for halogen binding.

In another embodiment of the invention a recombinant antibody or antigen binding fragment comprises an amino acid sequence having 80-100% sequence identity, e.g. at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 4, 5 or 6. In some embodiments, an antibody or antigen binding fragment according to the present invention comprises heavy and light chain variable regions comprising amino acid sequences having 80-100% sequence identity, e.g. at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3 and SEQ ID NO: 4, or to SEQ ID NO: 5 and SEQ ID NO: 6, or to SEQ ID NO: 3 and SEQ ID NO: 6, or to SEQ ID NO: 5 and SEQ ID NO: 4. In a further embodiment of the invention an isolated nucleic acid molecule encoding the antibody or antigen binding fragment of the present invention comprises a polynucleotide sequence having 80-100% sequence identity, e.g. at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 1, 2, 7 or 8. In a specific embodiment an isolated nucleic acid molecule encoding the antibody or antigen binding fragment of the present invention comprises a polynucleotide sequence having 80-100% sequence identity, e.g. at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 1 and 2, or SEQ ID NO: 7 and 8.

In one embodiment of the invention the light chain of the recombinant antibody or antigen binding fragment comprises an amino acid sequence having 80-100 (e.g. at least 90%, 91%, 92%, 93%, 94%, 95%, 96%, 97%, 98%, 99%) sequence identity to amino acids 1-109 of SEQ ID NO: 3 or SEQ ID NO: 5, and/or the heavy chain of the recombinant antibody or antigen binding fragment comprises an amino acid sequence having 80-100% (e.g. at least 90%, 91%, 92%, 93%, 94%, 95%, 96%, 97%, 98%, 99%) sequence identity to amino acids 1-124 of SEQ ID NO: 4 or SEQ ID NO: 6.

Identity of any sequence or fragments thereof compared to the sequence of this disclosure refers to the identity of any sequence compared to the entire sequence of the present invention. As used herein, the % identity between the two sequences is a function of the number of identical positions shared by the sequences (i.e. identity=# of identical positions/total # of positions×100), taking into account the number of gaps, and the length of each gap, which need to be introduced for optimal alignment of the two sequences. The comparison of sequences and determination of identity percentage between two sequences can be accomplished using mathematical algorithms available in the art. This applies to both amino acid and nucleic acid sequences. As an example sequence identity may be determined by using BLAST (Basic Local Alignment Search Tools) or FASTA (FAST-All). In the searches, setting parameters "gap penalties" and "matrix" are typically selected as default.

In one embodiment of the present invention the recombinant antibody is a monoclonal antibody or the antigen binding fragment is a single chain Fv or Fab fragment. In a specific embodiment the antigen binding fragment is a single chain Fv or Fab fragment comprising one or more CDRs selected from the group consisting of light chain CDRs 1-3 comprising amino acids 24-33, 49-55, and 88-96 of SEQ ID NO:3, respectively, and heavy chain CDRs 1-3 comprising amino acids 31-35, 50-66, and 99-113 of SEQ ID NO:4, respectively. In a specific embodiment the antigen binding fragment is a single chain Fv or Fab fragment comprising one or more CDRs selected from the group consisting of light chain CDRs 1-3 comprising amino acids 24-33, 49-55, and 88-96 of SEQ ID NO:5, respectively, and heavy chain CDRs 1-3 comprising amino acids 31-35, 50-66, and 99-113 of SEQ ID NO:6, respectively. In a more specific embodiment a single chain Fv or Fab fragment comprises or consists of amino acid sequences of SEQ ID NO: 3 and/or 4, SEQ ID NO: 5 and/or 6, SEQ ID NO: 3 and/or 6, or SEQ ID NO: 5 and/or 4.

In a very specific embodiment of the invention the light chain of the antibody or antigen binding fragment is a kappa (κ) type chain.

In specific embodiments of the present invention the antibody or antigen binding fragment is a fusion polypeptide, i.e. may have been fused (e.g. by genetic engineering) with e.g. any other fragments or polypeptides to form a fusion polypeptide. Examples of suitable fusion partners include any conventional fusion partners known to a person skilled in the art, e.g. including but not limited to alkaline phosphatase, hydrophobin and any peptide suitable for functionalization.

In one embodiment of the present invention the recombinant antibody or antigen binding fragment binds to human or animal T4 thyroid hormone. Indeed, the recombinant antibody or antigen binding fragment is able to recognize an epitope of T4 thyroid hormone.

In one embodiment of the invention the recombinant antibody or antigen binding fragment has an affinity of 800 pM or less (e.g. 10-800 pM or 30-600 pM or 200-530 pM, or 600 pM or less, or 530 pM or less) towards T4 thyroid hormone (e.g. when measured by competition ELISA and/or SPR sensors e.g. as described in the article of Tullila and Nevanen 2017, International Journal of Molecular Sciences 18(6), 1169). In another embodiment the recombinant antibody or antigen binding fragment has an affinity of 800 nM or less (e.g. 10-800 nM, 30-600 nM or 37-558 nM, or 600 nM or less, or 558 nM or less) towards halogenated bisphenol A (e.g. depending on the halogen (iodine, bromine or chloride)) (e.g. when measured by competition ELISA and/or SPR sensors e.g. as described in the article of Tullila and Nevanen, 2017, International Journal of Molecular Sciences 18(6), 1169). In a further embodiment of the invention the recombinant antibody or antigen binding fragment has an affinity of 800 pM or less (e.g. 10-800 pM or 30-600 pM or 200-530 pM, or 600 pM or less, or 530 pM or less) towards T4 thyroid hormone and an affinity of 800 nM or less (e.g. 10-800 nM, 30-600 nM or 37-558 nM, or 600 nM or less, or 558 nM or less) towards halogenated bisphenol A depending on the halogen (iodine, bromine or chloride). In a very specific embodiment of the invention the affinity is measured by utilizing the inhibition method (e.g. by utilizing Biacore 200T equipment) e.g. as described in the article of Tullila and Nevanen (2017, International Journal of Molecular Sciences 18(6), 1169). In a very specific embodiment the KD values of the recombinant antibody or antigen binding fragment are as follows: T4 less than 0.6+/−0.04 nM (e.g. 0.53+/−0.04 nM), halogenated bisphenol A less than 560+/−0.04 nM, less than 70+/−1.9 nM or less than 40+/−1.8 nM (e.g. Tetraiodobisphenol A (TIBPA) less than 40+/−1.8 nM (e.g. 37.3+/−21 nM), Tetrabromobisphenol A (TBBPA) less than 70+/−1.9 nM (e.g. 69.2+/−1.9 nM) and/or Tetrachlorobisphenol A (TCBPA) less than 560+/−21 nM (e.g. 558+/−21 nM)). In one embodiment of the invention KD is measured by competition ELISA and/or SPR sensors e.g. as described in the article of Tullila and Nevanen (2017, International Journal of Molecular Sciences 18(6), 1169) or by utilizing Biacore 200T equipment e.g. as described in the article of Tullila and Nevanen (2017, International Journal of Molecular Sciences 18(6), 1169).

In one embodiment the recombinant antibody or antigen binding fragment of the invention has cross reactivity to T3 and/or T2. In a very specific embodiment the KD values of the recombinant antibody or antigen binding fragment are as follows: T3 30+/−0.4 nM or less, 25+/−0.4 nM or less, or 21+/−0.4 nM or less (e.g. 20.8+/−0.4 nM) and/or T2 1850+/−21 nM or less (e.g. 1810+/−21 nM). In a very specific embodiment of the invention the cross reactivity is measured by utilizing the inhibition method (e.g. Biacore T 200 equipment) e.g. as described in the article of Tullila and Nevanen (2017, International Journal of Molecular Sciences 18(6), 1169). As used herein "cross reactivity" refers to a reaction between an antibody or antigen binding fragment and an antigen other than the most specific antigen (T4) to said antibody or antigen binding fragment. Indeed, cross-reactivity measures the extent to which different antigens appear similar to an antibody or an antigen binding fragment.

In some embodiments of the present invention the antibody or antigen binding region (e.g. a single chain Fv or Fab fragment) is capable of binding T4 thyroid hormone with a relative $IC_{50}$ equal or less than 0.70 nM (e.g. 0.60 nM or less, or 0.54 nM or less (e.g. 0.54 nM by ELISA assay)). In other embodiments the antibody or antigen binding region is capable of binding halogenated bisphenol A with a relative $IC_{50}$ equal or less than 560 nM (e.g. 550 nM or less, 75 nM or less, 55 nM or less (e.g. TIBPA 54 nM, TBBPA 74 nM, TCBPA 544 nM by ELISA assay)). As an example, $IC_{50}$ values for T4 and tetrahalobisphenol A may be 0.50-0.60 nM (e.g. 0.53 nM) and 37-558 nM respectively, depending on the halogen. In a very specific embodiment of the invention $IC_{50}$ value is measured by utilizing the inhibition method (Biacore T200 equipment) e.g. as described in the article of Tullila and Nevanen (2017, International Journal of Molecular Sciences 18(6), 1169). In competition binding assays the $IC_{50}$ is the concentration of competing ligand which displaces 50% of the specific binding to the immobilized T4-AP conjugate. In competition binding assays, a single concentration of an antibody is used in every assay tube. The ligand is used at a low concentration, usually at or below its $K_d$ value. The level of specific binding of the antibody is then determined in the presence of a range of concentrations of the competing compounds, in order to measure the potency with which they compete for the binding of the antibody. Competition curves may also be computer-fitted to a logistic function. The $IC_{50}$ value may be converted to an absolute inhibition constant $K_i$ using the Cheng-Prusoff equation.

Advantages of the present invention are at least high affinity and unique specificity. In one embodiment "high affinity" refers to an affinity of 800 pM or less (more specifically e.g. 600 pM or less, or 530 pM or less) towards T4 thyroid hormone (e.g. when measured by utilizing the inhibition method (Biacore T200 equipment) e.g. as described in the article of Tullila and Nevanen (2017) as described earlier in the disclosure. As used herein "specificity" refers to a degree revealing how the recombinant antibody or antigen binding fragment of the present invention is able to detect a target molecule of interest, i.e. T4, in relation to the other thyroid hormones and halogenated bisphenol A's (e.g. tetrahalobisphenol A's). As used herein "unique specificity" refers to a specific specificity value of the present invention e.g. when measured by utilizing the inhibition method (Biacore T200) e.g. as described in the article of Tullila and Nevanen (2017). In a very specific embodiment of the invention the recombinant antibody or antigen binding fragment has an affinity of 800 pM or less (e.g. 10-800 pM or 30-600 pM or 200-530 pM, or 600 pM or less, or 530 pM or less) towards T4 thyroid hormone, and cross reactivity to T3 or T2 with KD values T3 30+/−0.4 nM or less, and/or T2 1850+/−21 nM or less, or capability to bind T4 thyroid hormone with a relative $IC_{50}$ equal or less than 0.70 nM. In a more specific embodiment of the invention the recombinant antibody or antigen binding fragment has an affinity of 800 pM or less (e.g. 10-800 pM or 30-600 pM or 200-530 pM, or 600 pM or less, or 530 pM or less) towards T4 thyroid hormone; and cross reactivity to T3 or T2 with KD values T3 30+/−0.4 nM or less, and/or T2 1850+/−21 nM or less; and capability to bind T4 thyroid hormone with a relative $IC_{50}$ equal or less than 0.70 nM.

Mammalian cell lines are widely used expression systems for the production of recombinant antibodies. Bacteria, yeasts, filamentous fungi, plant and insect cells can also be employed for the production of recombinant antibodies in order to lower the production costs in cases wherein the glycosylation pattern does not play a critical role (e.g. in vitro diagnostics). Therefore, a host cell comprising the recombinant nucleic acid molecule encoding the antibody or antigen binding fragment or the expression vector comprising the recombinant nucleic acid molecule is not limited to but may be selected e.g. from the group consisting of eukaryotic or prokaryotic cell, bacteria, yeasts, filamentous fungi, and animal, human, mammalign, plant and insect cell lines. It may even be a hybridoma cell, which after transformation produces a recombinant monoclonal antibody.

Recombinant antibodies or antigen binding fragments can be developed e.g. by using genetically engineered genes expressed in an in vitro cell lines or by traditional hybridoma based technologies. The recombinant antibody or antigen binding fragment may also be produced synthetically. All these techniques for producing recombinant antibodies are known to a person skilled in the art and described in practical manuals and handbooks describing laboratory molecular techniques. Recombinant techniques in producing antibodies or antigen binding fragments enable production of identical antibodies in each manufacturing batch. Furthermore, the manufacturing process gives high purity and ultra-low batch-to-batch variability.

In one embodiment of the invention the method of producing a recombinant antibody or antigen binding fragment for binding T4 thyroid hormone comprises introducing an expression vector comprising the nucleic acid molecule encoding the antibody or antigen binding fragment of the present invention into a host cell and growing the cell under conditions permitting production of the antibody or antigen binding fragment, and optionally further recovering the produced antibody or antigen binding fragment.

The recombinant antibody or antigen binding fragment library is conveniently an expression library, which is typically a phage display library. The general principle of the display recombinant antibody or antigen binding fragment libraries is that they present the antigen binding fragment as a fusion protein on the surface, which may be the surface of a microbial cell such as a yeast or bacterial cell, or a bacteriophage. The display recombinant library can also be a display library, where stable complexes of nascent protein and mRNA are produced in an in vitro expression system. Phage display is the most frequently used display method for antibody libraries. The antibodies or antigen binding fragments are conveniently discovered from a recombinant phage display antibody library.

A phage display antibody library may be constructed by antibody fragment coding DNAs into an appropriate phage display vector.

DNA encoding for millions of variants of antibody fragments is batch-cloned into the vector as part of the phage coat protein. Large libraries containing millions of antibody fragments with different specificities can be obtained by transforming the vectors to bacteria. Cultivation of the bacteria leads to the expression of phages displaying antibody fragments on the surface of the phages. The gene for the displayed antibody is carried in the phagemid plasmid packed inside the phage, thus linking genotype with phenotype. The physical linkage between the displayed protein and its DNA allows screening of vast numbers of variants of the protein, each linked to its corresponding DNA, by a simple in vitro selection procedure called panning.

In its simplest form, panning may be carried out by incubating the pool of phage displayed variants with the antigen or ligand of interest that has been immobilized on a carrier, washing away unbound phage, and eluting specifically bound phage by disrupting the binding to the ligand. The eluted phage is then amplified in vivo.

The process is repeated several times, resulting in stepwise enrichment of the phage pool in favour of the tightest binding sequences. After about 3 to 6 rounds of selection followed by a screening assay for individual antibody clones, the best clones are sequenced and the diversity of the binders is examined.

The present invention relates to a novel T4 thyroid hormone specific recombinant antibody. Benefits of the recombinant antibodies include reduced size, efficient immobilization, and cheap bacterial production when compared to conventional monoclonal and polyclonal antibodies.

Antibody libraries enable in vitro selection of novel antibodies. Antibody libraries may contain ~$10^{6-9}$ different clones. Selection of recombinant antibody libraries can be carried out e.g. by automated magnetic bead processor. Several different selection methods can be used to select specific antibodies. Single recombinant antibody clones are screened e.g. by a high throughput robotic station. Preliminary characterization of the candidate antibodies is carried out e.g. by ELISA and sequence comparison.

A subset of strains containing antibodies has been deposited according to the Budapest Treaty on the International Recognition of the Deposit of Microorganisms for the Purposes of Patent Procedure, 1977, in VTT Culture Collection, P.O. Box 1000, FI-02044 VTT, FINLAND, (culturecollection.vtt.fi) with the following codes (E-number): T4 Fab/pKKtac/RV308; VTT E-173550.

The present invention also relates to a fast and simple assay for thyroid hormone (T4) (specific) and/or halogenated bisphenol A (specific) antibody and immunoassay in various diagnostics platforms and sensors. One aspect of the present invention concerns an immunoassay comprising the recombinant antibody or antigen binding fragment of the present invention. Also, the present invention concerns said immunoassay for use in a method of the present invention namely a method for determining T4 thyroid hormone and/or halogenated bisphenol A concentration(s) in a sample. In one embodiment of the invention said immunoassay further comprises additional reagents necessary for performing said immunoassay and/or instructions for performing said immunoassay. In one embodiment the immunoassay comprises reagents necessary for performing an immunoassay, such as one or more selected from the group consisting of reaction solutions, buffers, washing solutions and detection means, such as labels (e.g. enzyme labels).

Optionally control samples (e.g. positive or negative control samples) or reference levels revealing specific T4 thyroid hormone and/or halogenated bisphenol A levels or concentrations may also be included in the immunoassay of the present invention. Also, a quality control may optionally be comprised within the immunoassay. In a specific embodiment the immunoassay comprises instructions for carrying out an immunoassay for determining T4 thyroid hormone and/or halogenated bisphenol A concentrations of a sample.

In one embodiment the immunoassay is a competitive or non-competitive immunoassay. In another embodiment the method for determining T4 thyroid hormone and/or halogenated bisphenol A concentrations comprises or is a competitive or non-competitive immunoassay. Competitive immunoassays include homogenous (e.g. fluorescence polarisation assay) and heterogenous (e.g. competitive ELISA) immunoassays. In a competitive immunoassay, unlabelled analyte in a sample competes with labelled analyte to bind an antibody or antigen binding fragment. The amount of labelled, unbound analyte is then measured. The more analyte there is in the sample, the less labelled analyte is detected. As used herein "a noncompetitive immunoassay" refers to e.g. an immunocomplex assay (Pulli, Höyhtyä, Söderlund, Takkinen, 2005, Anal. Chem. 77, 2637-2642). In noncompetitive immunoassays the intensity of the signal is directly proportional to the amount of the analyte in the sample.

The label(s) optionally utilized in the present invention can be any conventional labels, such as a radioactive label, an enzyme, a nucleotide sequence or a fluorescent compound. The immunoassay is not limited to but can be selected e.g. from the group consisting of ELISA, immunoPCR or FIA. In one embodiment the immunoassay for T4 thyroid hormone and/or halogenated bisphenol A may be for example a conventional sandwich test in microtiter wells or a lateral flow-test. In another embodiment the antibody, antigen binding fragment and/or any of their engineered version included in the present invention are used in sensors based on immunoassays. Furthermore, any other assay types, such as agglutination test, lateral flow test, capillary electrophoresis, antibody arrays, cantilevers and/or microfluidic assay systems, or any combination thereof can be applied in the present invention. Indeed, the method for determining T4 thyroid hormone and/or halogenated bisphenol A concentrations may comprise use of one or more of said (immune)assays.

Detection mode of the method or immunoassay of the present invention can be any conventional detection mode including but not limited to colorimetric, fluorescent, paramagnetic, electrochemical or label free (e.g. surface plasmon resonance and quartz crystal microbalance) detection mode.

In the method of the present invention for determining T4 thyroid hormone and/or halogenated bisphenol A concentration(s) in a sample the recombinant antibody or antigen binding fragment is allowed to contact with a sample e.g. in an immunoassay as described above. Determination of the level or amount of T4 thyroid hormones and/or halogenated bisphenol A in a sample may be carried out e.g. based on the colorimetric, fluorescent, paramagnetic, electrochemical or label free (e.g. surface plasmon resonance and quartz crystal microbalance) detection mode. Optionally determination may also comprise use of any suitable statistical methods known to a person skilled in the art.

The present invention also concerns a test kit comprising the recombinant antibody or antigen binding fragment of the present invention. Also, the present invention concerns said test kit for use in a method of the present invention. In one embodiment of the invention the test kit may further comprise one or more reagents for performing a test, and optionally instructions for use or performing a test. In one embodiment the test kit comprises one or several reagents selected from the group consisting of reaction solutions, buffers, washing solutions and detection means, such as labels and a fluorometer. In a specific embodiment of the present invention, the test kit comprises at least an enzyme label. In one embodiment said test kit is an immunoassay kit, and in a further embodiment said immunoassay is a competitive or non-competitive immunoassay. In a very specific embodiment the test kit comprises reagents for performing said immunoassay and/or instructions for performing said immunoassay.

In a specific embodiment the antibody or antigen binding fragment included in the immunoassay or test kit comprises the complementary determining regions (CDRs) of an antibody light chain and heavy chain, wherein said light chain CDR regions comprise or have the amino acid sequences of amino acids 24-33, 49-55, and 88-96 of SEQ ID NO:3 or SEQ ID NO:5, and said heavy chain CDR regions have the amino acid sequences of amino acids 31-35, 50-66, and 99-113 of SEQ ID NO:4 or SEQ ID NO:6.

Optionally control samples (e.g. positive or negative control samples) or reference levels revealing specific T4 thyroid hormone and/or halogenated bisphenol A levels may also be utilized in the present invention. Also, a quality control may optionally be comprised within the test kit. In a specific embodiment the test kit comprises instructions for carrying out a method for determining T4 thyroid hormone and/or halogenated bisphenol concentration(s) of a sample.

The performance of the assay or test may be such that the reagents (at least antibody or antigen binding fragment) are pre-dried in the well of a microtiter plate and a dilution series of at least one sample is added to the well. In such a case the test kit may comprise multiple reagent pairs physically separated from each other e.g. in the form of a microarray, whereby multiple antigens may be tested simultaneously from a sample. The assay or test kit of the present invention may also be applied to high through-put assays for large number of samples.

In a specific embodiment the present invention can be applied in the fast diagnostics of T4 thyroid hormone and/or halogenated bisphenol A e.g. in clinical human or animal samples. As used herein "fast diagnostics" refers to at least immunoassays (such as ELISA), lateral flow assays, sensor solutions and similar applications known to a skilled person and allowing.

In one embodiment T4 thyroid hormone and/or halogenated bisphenol A levels are determined in vitro from a sample such as a sample obtained from a subject or any biological sample. In one embodiment of the invention the sample is a biological, environmental, material or food sample, or a sample of a subject. In one embodiment of the invention a subject is a human or an animal, a child, an adolescent or an adult. Also any animal, such as a pet, domestic animal or production animal, may be a subject of the present invention. The sample obtained from a subject includes but is not limited to a sample of blood, serum, plasma, urine, tears, sweat, secretion, biopsy or tissue.

In one embodiment the recombinant antibody, antigen binding fragment or immunoassay of the present invention may be used for screening endocrine disruptor potential related to the thyroid axis present in a sample. As used herein "thyroid axis" refers to a part of the neuroendocrine system and as its name suggests, it depends upon the thyroid gland. The thyroid axis regulates development, energy metabolism, and growth and the axis is controlled by complex central and peripheral signals mediated mainly by hypothalamic thyrotropin-releasing hormone (TRH) and pituitary thyroid-stimulating hormone (TSH).

Before classifying a human or animal as suitable for determining T4 thyroid hormone and/or halogenated bisphenol A levels according to the present invention, the clinician may or may not carry out other medical assessments or analysis. For example any other biomarkers or levels thereof may be assayed before, simultaneously or after the method or assay of the present invention. After these preliminary studies and e.g. based on the results deviating from the normal, the clinician may suggest a method or assay of the present invention for a subject. Alternatively, the method and assay of the present invention are suitable for screening small groups of samples as well as samples of large populations.

Herein, the terms "polypeptide" and "protein" are used interchangeably to refer to polymers of amino acids of any length.

As used herein "polynucleotide" refers to any polynucleotide, such as single or double-stranded DNA (genomic DNA or cDNA) or RNA, comprising a nucleic acid sequence encoding a polymer of amino acids or a polypeptide in question or a conservative sequence variant thereof. Conservative nucleotide sequence variants (i.e. nucleotide sequence modifications, which do not significantly alter biological properties of the encoded polypeptide) include variants arising from the degeneration of the genetic code and from silent mutations.

Minor variations or modifications of any one of the sequences or subsequences set forth in the description and claims are still within the scope of the invention provided that they do not affect the binding activity and/or affinity of the antibody or antigen binding fragment. Methods for making any genetic modifications are generally well known and are described in various practical manuals describing laboratory molecular techniques.

In general the presence, absence or amount of T4 polypeptides (or activities thereof) or polynucleotides in a sample can be detected by any suitable method known in the art. Non-limiting examples of suitable detection methods include enzymatic assays, PCR based assays (e.g., qPCR, RT-PCR), immunological detection methods and combinations thereof.

The following examples are given to further illustrate embodiments of the present invention but are not intended to limit the scope of the invention. It will be obvious to a person skilled in the art that, as the technology advances, the inventive concept can be implemented in various ways. The invention and its embodiments are not limited to the examples described below but may vary within the scope of the claims.

EXAMPLES

Example 1. Construction of the Antibody Gene Library, Selection and Screening of Anti-T4 Antibodies A mouse was multi-immunized with T4- and T3-Blue-Carrier® conjugates in Freund's adjuvant. The library was constructed and propagated to a surface of bacterial phages as described in Tullila and Nevanen (2017, International Journal of Molecular Sciences, 18(6), 1169). T4-AP was biotinylated with sulfo-NHS-SS-biotin reagent following manufacturer's instructions (Thermo Fisher Scientific, Waltham, Mass., USA). Biotinylated T4-AP was incubated with Fab fragment phage display library and captured with Streptavidin coupled SpeedBeads (Thermo Fisher Scientific, Waltham, Mass., USA). Magnetic particles were washed with PBST and bound phages eluted by DTT. Total of four selection rounds were performed prior to the initiation of single clones screening.

Total of 384 single colonies were picked from LB-amp plates onto 96-well micro-titerplates containing 100 µl of SB-cultivation media supplemented with 100 µg/ml ampicillin, 10 µg/ml tetracycline and +1% (w/v) glucose using. On the following day 9 µl of overnight cultures were added to 100 µl of SB containing 100 µg/ml ampicillin, 10 µg/ml tetracyclin, 0.1% glucose and 1 mM isopropyl-beta-D-thiogalacto-pyranoside (IPTG, Sigma-Aldrich, St. Louis, Mo., USA)/well) and grown overnight at 34° C. in 80% humidity with shaking. For the ELISA screening assays 300 ng of T4-HSA in Na-bicarbonate buffer pH 9.6 was coated onto each well of MaxiSorp-plates (Nunc) for overnight at +4° C. On the following day plates were washed with PBST, blocked with SuperBlock® (Thermo Fisher Scientific) for 30 minutes and washed again. Antibody containing culture supernatants were diluted 1:1 in SuperBlock® and 100 µl were transferred into each well. Samples were incubated in for 1 hour after which the wells were washed as previously. 100 µl of 1:2000 diluted anti-mouse Kappa-AP (Southern Biotech) in SuperBlock® was added to wells, incubated for 1 hour and washed as previously. Detection was carried out by adding 100 µl of 2 mg/ml p-Nitrophenyl Phosphate (pNPP, Sigma-Aldrich) in Diethanolamine-MgCl$_2$ (Reagena, Toivala, Finland) to each well. Wells were read at A405 after 30 minutes of enzyme reaction with plate reader (Beckmann Coulter DTX 880 multimode detector). The clone (T4) giving highest intensities against T4- and T3-HSA coated wells was chosen for further characterization.

The antibody coding insert was transferred into pKKtac expression vector (Takkinen, K. et al., Protein Engineering, Design and Selection, 4(7), 837-841) that included Hiss-tag at the C-terminal position of the Fab heavy chain. Construct was further transferred into RV308 *E. coli* strain (ATCC 31608), and T4 Fab fragment antibody was produced and purified as described in Tullila and Nevanen (2017, International Journal of Molecular Sciences, 18(6), 1169) (See FIGS. 1A (SEQ ID NO: 1), 1B (SEQ ID NO: 2), 2A (SEQ ID NO: 3) and 2B (SEQ ID NO: 4)).

Example 2. Affinity and Specificity Determination

Affinities of purified anti-T4 Fab fragment to various analytes were analysed using a surface plasmon resonance instrument BIAcore T200 (GE Healthcare, Piscataway, N.J., USA) with inhibition assay (Nieba, L. et al. 1996, Anal. Biochem. 234, 155-165; Badescu, G. O. et al. 2016, PLoS ONE, 11, e0152148; Persson, B. D. et al. 2009, J. Virol. 83, 673-686; Tullila, A., and Nevanen, T. K. 2017, International Journal of Molecular Sciences, 18(6), 1169; Adamczyk, M. et al. 1998, Bioconjugate chemistry, 9(1), 23-32. Prior to the immobilization, the surface of BIAcore CM5 sensor chip (29104988, GE Healthcare, Piscataway, N.J., USA) was preconditioned as described by Cannon et al. (2004, Analytical biochemistry, 330.1: 98-113). T4-AP and AP (P5931, Sigma-Aldrich, St. Louis, Mo., USA), were diluted to 100 µg/mL concentration in 10 mM sodium acetate pH 4.0 (BR100351, GE Healthcare, Piscataway, N.J., USA). T4-AP and AP were immobilized to preconditioned CM5 chip using EDC/NHS—chemistry following manufacturer's instructions. Concentration of anti-T4 Fab fragment was calculated using theoretical extinction coefficient (ExPASy ProtParam tool, web.expasy.org/protparam) of the anti-T4 Fab fragment and by measuring the A280 with NanoDrop 2000c instrument (Thermo Disher Scientific, Waltham, Mass., USA). 4 nM anti-T4 Fab fragment was prepared into 2% (v/v) DMSO-PBSP (20 mM phosphatase, 2.7 mM KCl, 137 mM NaCl, 0.05% Tween 20 (prepared from 10×PBSP+, 28-9950-84, GE Healthcare, Piscataway, N.J., USA) supplemented with DMSO (D5897, Sigma-Aldrich, St. Louis, Mo., USA) and further diluted 3/5 fold into same buffer to obtain a calibration series of free Fab fragment antibody. Total of eight dilutions were used in each analysis. Contact time for association was set to 420 seconds and for dissociation to 30 seconds. Successful regeneration of anti-T4 Fab was achieved with 10 mM NaOH supplemented with 0.05% (v/v) P20. Flowrate was set to 30 µl/min in all cycle steps.

Figure 4A:
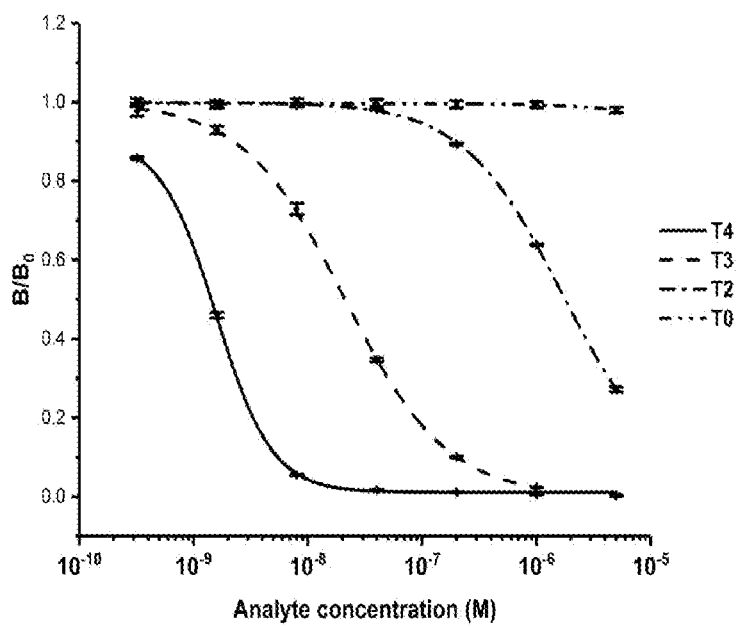
FIG. 4 shows affinity and specificity data for T4 Fab determined by Surface Plasmon Resonance (SPR). T4-alkaline phosphatase was immobilized to the sensor surface and Kd values were determined by inhibition assay method.
Figure 4B:
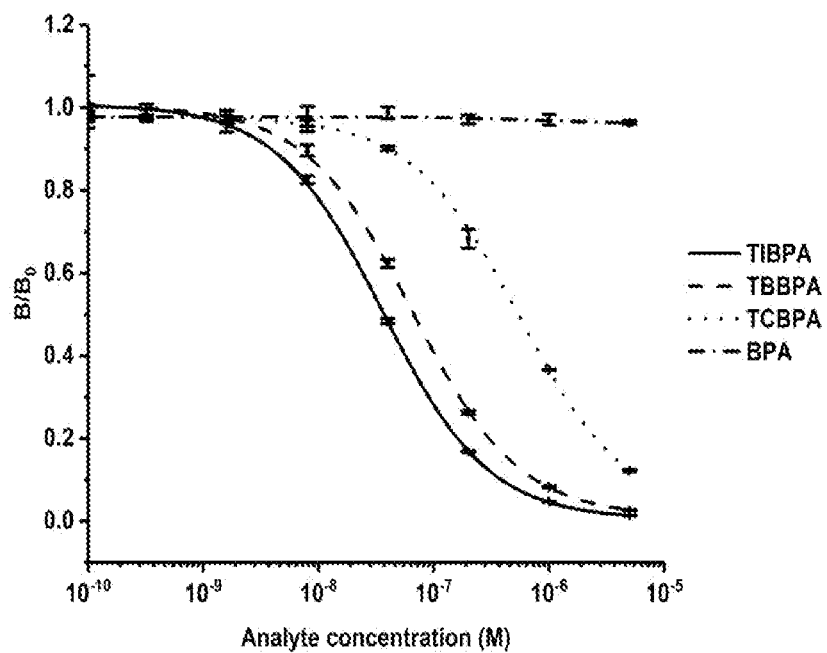

Varying concentrations of analytes T4 (T2376, Sigma-Aldrich, St. Louis, Mo., USA), T3 (T2877, Sigma-Aldrich, St. Louis, Mo., USA), T2 (D0629, Sigma-Aldrich, St. Louis, Mo., USA), T0 (T5905, Sigma-Aldrich, St. Louis, Mo., USA), Tetraiodobisphenol A (4971-59-9, Spectra Group Limited), Tetrabromobisphenol A (330396, Sigma-Aldrich St. Louis, Mo., USA), Tetrachlorobisphenol A (TCI-T0062, Tokio Chemical Industry) and Bisphenol A (239658, Sigma-Aldrich, St. Louis, Mo., USA) were preincubated with 2 nM concentration of anti-T4 Fab fragment. Preincubated mixtures were injected over the sensor chip surface for seven minutes and dissociated for 30 seconds. Bound anti-T4 Fab fragments were successfully regenerated from the surface with 10 mM NaOH+0.05% (v/v) Tween20. Data collection point was set to be 10 seconds after the start of dissociation phase. All sample series were run as triplicates, where a single sample series consisted from growing small molecule concentration in the preincubation mixture. Data was reference and blank subtracted. In addition, small differences in DMSO between the samples were compensated using DMSO solvent correction series, as recommended by instrument manufacturer GE Healthcare). Concentrations of free anti-T4 Fab fragments remaining in the preincubated mixtures were calculated by comparing the obtained responses against standard curve of anti-T4 Fab fragment. Affinity constants were calculated using BIAcore T200 Evaluation Software (GE Healthcare, Piscataway, N.J., USA) applying four-parameter logistic function. (See FIGS. 4A and B and Table 1.)

TABLE 1

Affinity constants using BIAcore T200 Evaluation Software.

| Compound | anti-T4 Fab $K_D$ (nM) |
|---|---|
| T4 | 0.53 ± 0.04 |
| T3 | 20.8 ± 0.4 |
| T2 | 1810 ± 21 |
| T0 | no binding |
| TIBPA | 37.3 ± 1.8 |
| TBBPA | 69.2 ± 1.9 |
| TCBPA | 558 ± 21 |
| BPA | no binding |

Example 3. ELISA Assays

L-Thyroxine

Microtiter plate wells (Nunc, 436023) were coated with 100 μl of 4 μg/ml T4-BSA (Fitzgerald, 80-IT50) in PBS (15 mM phosphate, 150 mM NaCl, pH 7.3) for one hour at +37° C. with 600 rpm shaking. Wells were then washed three times with 300 μl PBS supplemented with 0.05% (v/v) Tween20 (Sigma-Aldrich, 93773-250G). Wells were blocked with 200 μl of Superblock® (Thermo Fisher Scientific, 37516) for 30 minutes in room temperature with 600 rpm shaking and washed as above. 100 μl of pre-incubated mixtures, containing 0.25 nM anti-T4 Fab and varying concentrations of L-thyroxine (T4) (Sigma-Aldrich, T2376) in PBSP (GE Healthcare, 28-9950-84) supplemented with 1% DMSO (v/v) (Sigma-Aldrich, D5879-100ML), were transferred to wells and incubated for 30 minutes with 600 rpm shaking in room temperature. Each sample had 12 replicates. Wells were washed as above and 100 μl of Goat anti-mouse Kappa-HRP (SoutherBiotech, 1050-05) diluted 1:1000 in Superblock was transferred to wells and incubation was carried out for 30 minutes at 600 rpm shaking in room temperature. Wells were washed as above and 100 μl of TMB Microwell Peroxidase Substrate System (2-C) (SeraCare, 50-76-00) was transferred to wells and enzymatic reaction was carried out for 30 minutes with 600 rpm shaking in room temperature. Reactions were stopped by transferring 100 μl of 1 M $H_3PO_4$ to the wells and measured at A450 using Varioskan (Thermo Fisher Scientific). Data was analysed with OriginPro 2017-software.

Figure 5:
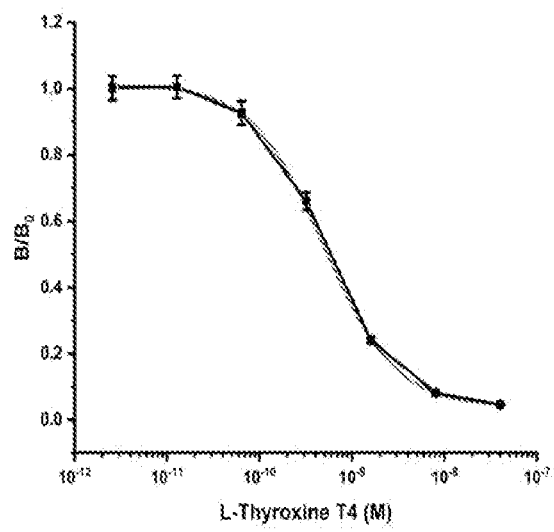
FIG. 5 reveals the results of the ELISA assay for L-thyroxine.

As seen in the FIG. 5, in competitive ELISA assay the Limit of detection (LOD) value is 84 pM and Limit of quantification (LOQ) is 314 pM indicating the potential of the T4 Fab for the measurement of the total thyroxine concentration in a sample (see FIG. 5 for the results.)

Tetraiodobisphenol A

Assay was performed as in the previous paragraph (under title L-Thyroxine) except instead of T4 (Thyroxine) TIBPA (Tetraiodobisphenol A) was used.

Figure 6:
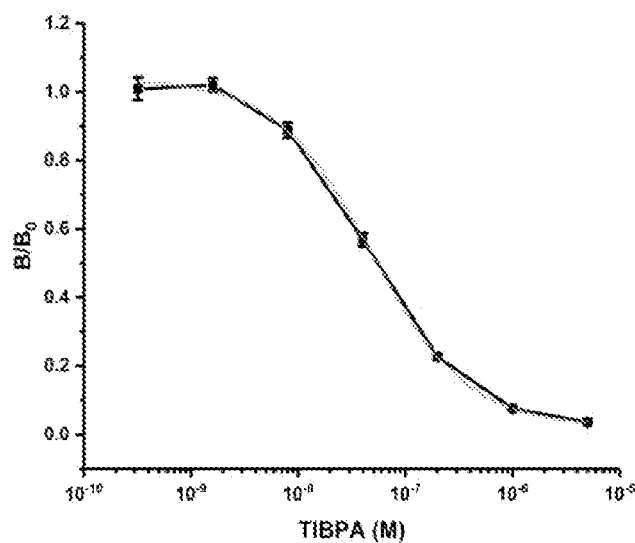
FIG. 6 reveals the results of the ELISA assay for Tetraiodobisphenol A.

The competitive ELISA results for LOD and LOQ are comparable with the Biacore affinity measurements. The sensitivity of the competitive ELISA assay for TIBPA is two orders of magnitude less than for L-thyroxine. For the results see FIG. 6.

Tetrabromobisphenol A

Assay was performed as in the paragraph under title L-Thyroxine except instead of T4 (Thyroxine) TBBPA (Tetrabromobisphenol A) was used.

Figure 7:
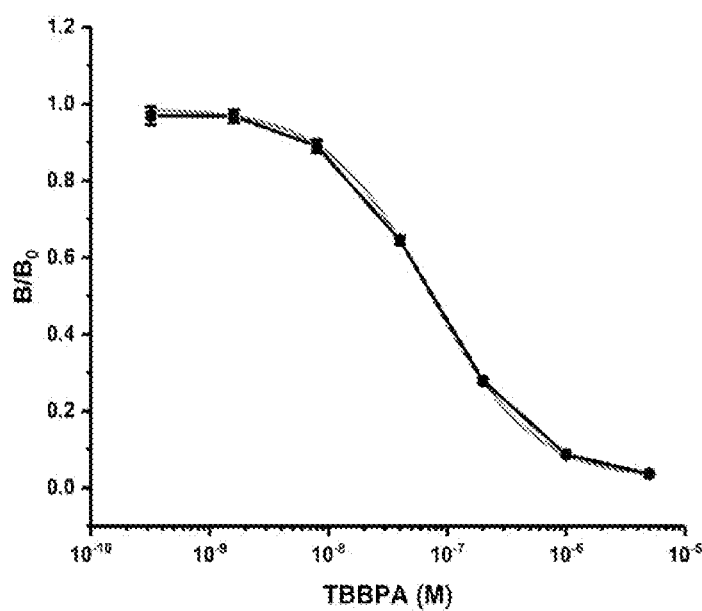
FIG. 7 reveals the results of the ELISA assay for Tetrabromobisphenol A.

The competitive ELISA results for LOD and LOQ are comparable with the Biacore affinity measurements. The sensitivity of the competitive ELISA assay for TBBPA is more than two orders of magnitude less than for L-thyroxine. For the results see FIG. 7.

Tetrachlorobisphenol A

Assay was performed as in the paragraph under title L-Thyroxine except instead of T4 (Thyroxine) TCBPA (Tetrachlorobisphenol A) was used.

Figure 8:
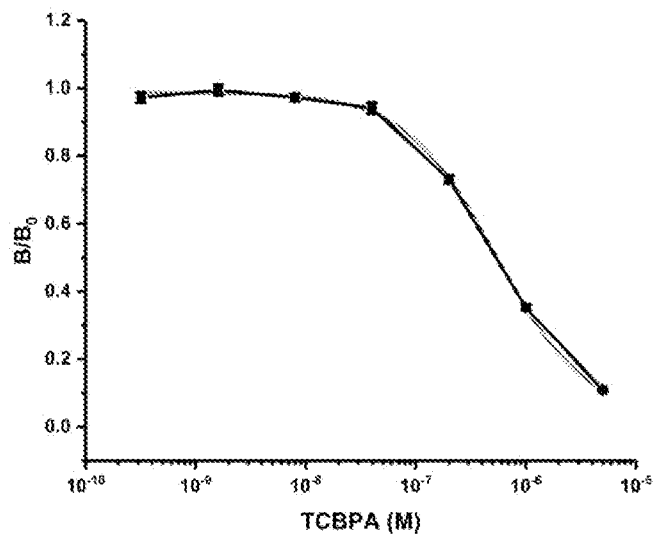
FIG. 8 reveals the results of the ELISA assay for Tetrachlorobisphenol A.

The competitive ELISA results for LOD and LOQ are comparable with the Biacore affinity measurements. The sensitivity of the competitive ELISA assay for TCBPA is three orders of magnitude less than for L-thyroxine. For the results see FIG. 8.

Bisphenol A

Assay was performed as in the paragraph under title L-Thyroxine except instead of T4 (Thyroxine) BPA (Bisphenol A) was used.

Figure 9:
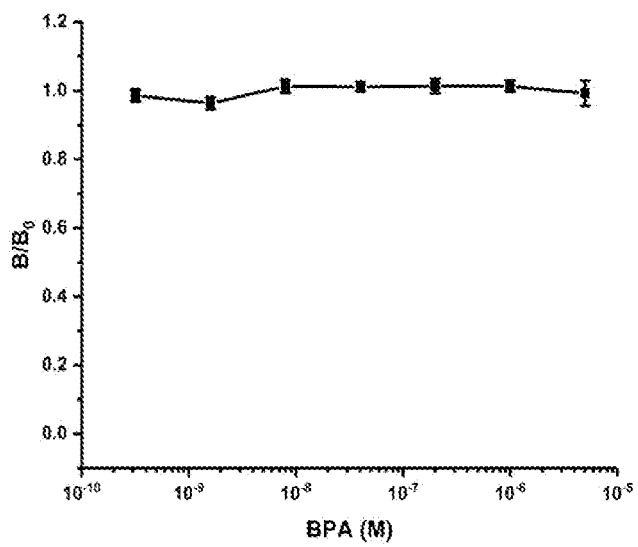
FIG. 9 reveals the results of the ELISA assay for bisphenol A.

No competition was observed even with high concentration (5 μM) of BPA in competitive ELISA assay. For the results see FIG. 9.

Example 4. Three-Dimensional Structure of Anti-T4 Antibodies

Crystallization of T4-Fab with T4 was carried out with vapor diffusion in hanging drops composed of 2 μl of the T4-Fab (4 mg/ml, incubated beforehand with T4) and 2 μl of reservoir solution. Initial crystals of the T4-Fab/T4 complex were obtained at 20° C. in reservoir solution conditions of 0.1 M ammonium sulfate, 0.1 M HEPES, pH 7.2, and 25% (w/v) PEG 3350. Streak seeding were used to improve the crystal quality. The crystals were cryoprotected by soaking in the crystallization solution supplemented with 20% glycerol and subsequently flash frozen in liquid nitrogen. The data for the T4-Fab/T4 complex structure was collected at 100 K on beamline I04 at the Diamond synchrotron and on beamline ID23 at ESRF (Grenoble, France), respectively. Data seta was processed with XDS (Kabsch) and scaled with XSCALE. The crystal belonged to space group C2 and had one molecule per asymmetric unit. The 1.9 Å resolution structure of T4-Fab/T4 was solved by molecular replacement with PHASER (McCoy, A. J. et al. *J. Appl. Cryst.* 40, 658-674 (2007)), by using coordinates of Fab hGR-2 F6 (PDB-code 1DQD) as search model. Several cycles of building and refinement were performed with COOT (Emsley, P., Lohkamp, B., Scott, W. G. & Cowtan, K. *Acta Cryst. D* 66, 486-501 (2010)) and PHENIX (Adams, P. D. et al. *Acta Cryst. D*, 66, 213-221 (2010)).

Three-dimensional structure was inspected with an appropriate molecular graphics software. Overall structure T4-Fab complexed with T4 is shown in FIG. 11*a* and a detailed picture on the active site in FIG. 11*b*. FIG. 10*a* reveals interatomic distances up to 4.0 Å between the atoms of ligands and anti-T4 Fab indicating the molecular bases of T4 and TIBPA ligand binding. Detailed pictures of halogen bonding in the structure of anti-T4 Fab and T4 or tetraiodobisphenol A (TIBPA) are presented in FIG. 10*b* 1 and 2, respectively.

The invention claimed is:

1. A recombinant antibody or an antigen binding fragment for binding T4 thyroid hormone and halogenated bisphenol A, wherein said recombinant antibody or antigen binding fragment comprises the following CDR amino acids:
   amino acids 88-96 of SEQ ID NO:3 or SEQ ID NO: 5 (a light chain region 3);
   amino acids 31-35 of SEQ ID NO: 4 or SEQ ID NO:6 (a heavy chain region 1);
   amino acids 50-66 of SEQ ID NO:4 or SEQ ID NO:6 (a heavy chain region 2); and
   amino acids 99-113 of SEQ ID NO:4 or SEQ ID NO:6 (a heavy chain region 3),
   and wherein:
   Y93 or F93, and L95 of SEQ ID NO: 3 or SEQ ID NO:5, Y33 or F33, A50, Y59 or F59, D100, Y107 or F107, Y109 or F109, and M111 of SEQ ID NO: 4 or SEQ ID NO:6 are responsible for binding to T4.

2. The recombinant antibody or antigen binding fragment of claim 1, wherein the recombinant antibody or antigen binding fragment has an affinity of 530 pM or less towards T4 thyroid hormone.

3. The recombinant antibody or antigen binding fragment of claim 1, wherein the recombinant antibody or antigen binding fragment has an affinity of 600 nM or less towards halogenated bisphenol A.

4. The recombinant antibody or antigen binding fragment of claim 1, wherein the antigen binding fragment is a single chain Fv (scFv) or Fab fragment.

5. A method of producing a recombinant antibody or an antigen binding fragment thereof for binding T4 thyroid hormone and for binding halogenated bisphenol A of claim 1, wherein the method comprises introducing an expression vector comprising a nucleotide sequence that encodes the recombinant antibody or antigen binding fragment thereof of claim 1 into a host cell and growing the cell under conditions permitting production of the antibody or antigen binding fragment.

6. The method of claim 5, further comprising recovering the produced antibody or antigen binding fragment.

7. A test kit comprising the recombinant antibody or antigen binding fragment of claim 1 for binding T4 thyroid hormone and halogenated bisphenol A,
and reaction solutions and chemical labels for conducting an immunoassay; and
control samples.

8. A method for determining T4 thyroid hormone and/or halogenated bisphenol A concentration(s) in a sample, comprising allowing the recombinant antibody or antigen binding fragment of claim 1 to contact the sample and thereafter determining the concentration of the T4 thyroid hormone and/or halogenated bisphenol A, respectively, in said sample.

9. An immunoassay for detecting T4 thyroid hormone and/or halogenated bisphenol A from a sample, wherein the immunoassay is competitive or non-competitive immunoassay comprising a recombinant antibody or antigen binding fragment of claim 1 for binding T4 thyroid hormone and halogenated bisphenol A, and suitable reagents and labels for determination of T4 thyroid hormone or halogenated bisphenol A concentrations in the sample after contacting the sample with the recombinant antibody or antigen binding fragment.

10. A recombinant antibody or an antigen binding fragment for binding T4 thyroid hormone and halogenated bisphenol A, wherein said recombinant antibody or antigen binding fragment comprises the following CDR amino acids
amino acids 24-33 of SEQ ID NO:3 or SEQ ID NO:5 (a light chain region 1);
amino acids 49-55 of SEQ ID No:3 or SEQ ID NO:5 (a light chain region 2);
amino acids 88-96 if SEQ ID NO:3 or SEQ ID NO: 5 (a light chain region 3);
amino acids 31-35 of SEQ ID NO: 4 or SEQ ID NO:6 (a heavy chain region 1);
amino acids 50-66 of SEQ ID NO:4 or SEQ ID NO:6 (a heavy chain region 2); and
amino acids 99-113 of SEQ ID NO:4 or SEQ ID NO:6 (a heavy chain region 3).

11. The recombinant antibody or antigen binding fragment of claim 10, wherein the recombinant antibody or antigen binding fragment has an affinity of 530 pM or less towards T4 thyroid hormone.

12. The recombinant antibody or antigen binding fragment of claim 1, wherein the recombinant antibody or antigen binding fragment has an affinity of 600 nM or less towards halogenated bisphenol A.

* * * * *